US011576889B2

(12) United States Patent
Brugarolas et al.

(10) Patent No.: US 11,576,889 B2
(45) Date of Patent: Feb. 14, 2023

(54) METHODS OF IDENTIFYING AND TREATING PATIENTS WITH HIF-2 INHIBITOR RESISTANCE

(71) Applicant: THE BOARD OF REGENTS OF THE UNIVERSITY OF TEXAS SYSTEM, Austin, TX (US)

(72) Inventors: James B. Brugarolas, Irving, TX (US); Haley Hill, Seattle, WA (US); Tao Wang, Coppell, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 209 days.

(21) Appl. No.: 17/030,123

(22) Filed: Sep. 23, 2020

(65) Prior Publication Data
US 2021/0085634 A1 Mar. 25, 2021

Related U.S. Application Data

(60) Provisional application No. 62/904,268, filed on Sep. 23, 2019.

(51) Int. Cl.
A61K 31/135 (2006.01)
A61P 35/00 (2006.01)
A61K 31/275 (2006.01)
G01N 33/50 (2006.01)
A61K 45/06 (2006.01)

(52) U.S. Cl.
CPC ........ A61K 31/275 (2013.01); G01N 33/5011 (2013.01); G01N 33/5044 (2013.01); A61K 45/06 (2013.01)

(58) Field of Classification Search
CPC .............................. A61K 31/135; A61P 35/00
USPC ........................................................ 514/657
See application file for complete search history.

(56) References Cited

FOREIGN PATENT DOCUMENTS

| WO | 1997012040 A | 4/1997 |
|---|---|---|
| WO | 2011005580 A2 | 1/2011 |
| WO | 2017075276 A2 | 5/2017 |
| WO | 2017218675 A1 | 12/2017 |

OTHER PUBLICATIONS

Chen et al, "Targeting renal cell carcinoma with a HIF-2 antagonist", Nature, vol. 539, pp. 112-117, Nov. 3, 2016.
Cho et al, "On-target efficacy of HIF-2α antagonist in preclinical kidney cancer models", Nature, vol. 539, pp. 107-111, (2016).
Choueiri et al, "Systemic Therapy Metastatic Renal-Cell Carcinoma", The New England Journal of Medicine, vol. 376, No. 4, pp. 354-366, Jan. 26, 2017.
Courtney et al, "Phase I Dose-Escalation Trial of PT2385, a First-In-Class Hypoxia-Inducible Factor-2α Antagonist in Patients With Previously Treated Advanced Clear Cell Renal Cell Carcinoma", J Clin Oncol, vol. 36, No. 9, pp. 867-874, Mar. 20, 2018.
Finlay et al, "Discovery of a Potent and Selective EGFR Inhibitor (A2D9291) of Both Sensitizing and T790M Resistance Mutations That Spares the Wild Type Form of the Receptor", Journal of Medicinal Chemistry. vol. 57, pp. 8249-8267, (2014).
Gerlinger et al, "intratumor Heterogeneity and Branched Evolution Revealed by Muliregion Sequencing", The New England Journal of Medicine, vol. 366, pp. 883-892, Mar. 8, 2012.
Hu et al, "Differential Roles of Hypoxia-Inducibte Factor 1α (HIF-1α) and HIF-2α in Hypoxic Gene Regulation", Molecular and Cellular Biology, vol. 23, No. 24, pp. 9361-9374, Dec. 2003.
Kobayashi et al, "EGFR Exon 18 Mutations in Lung Cancer: Molecular Predictions of Augmented Sensitivity to Afatinib or Neratinib as Compared with First- or Third-Generation TKIs", Clinical Cancer Research, vol. 21, No. 23, pp. 5305-5313, Dec. 1, 2015.
Koehler et al, "A complex task? Direct modulation of transcription factors with small molecules", Current Opinion in Chemical Biology, vol. 14, No. 3, pp. 331-340, Jun. 2010.
Rankin et al, "Hypoxia-inducible factor-2 (HIF-2) regulates hepatic erythropoietin in vivo". The Journal of Clinical Investigation, vol. 117, No. 4, pp. 1068-1077, Apr. 2007.
Rogers et al, "Development of inhibitors of the OAS-B Doman of the HIF-α Transcription Factor", J. Med. Chem., vol. 56. No. 4, pp. 1739-1747, Jan. 30, 2013.
Scheuermann et al, "Allosteric Inhibition of Hypoxia inducibie Factor-2 with Small Molecules", Nature Chemical Biology, vol. 9, No. 4, pp. 271-276, Apr. 2013.
Scheuermann et al, "Artificial ligand binding within the HIF2α PAS-B domain of the HIF2 transcription factor", PNAS, vol. 106, No. 2, pp. 450-455, Jan. 13, 2009.
Scortegagna et al, "HIF-2{alpha} regulates murine hematopoietic development in an erythropoietin-dependent manner", Blood, vol. 105, pp. 3133-3140, Dec. 30, 2004.
Turajilic et al., "Deterministic Evoiutionary Trajectories Influence Primary Tumor Growth: TRACERx Renal", Cell, vol. 173, No. 3, pp. 595-610, Apr. 19, 2018.
Wallace et al, "A Small-Molecule Antagonist of HIF-2α Is Efficacious in Preclinical Models of Renal Cell Carcinoma", Cancer Research, vol. 76, No. 18, pp. 5491-5550, Sep. 15, 2016.
Wang et al, "ANNOVAR: functional annotation of genetic variants from high-throughput sequencing data", Nucleic Acids Research, vol. 38, No. 16, pp. 17, (2010).
Wang et al, "Probability of phenotypically detectable protein damage by ENU-induced mutations in the Mutagenetix database", Nature Communications, vol. 9, No. 44, pp. 1-10, (2018).

(Continued)

Primary Examiner — Raymond J Henley, III
(74) Attorney, Agent, or Firm — DLA Piper LLP US

(57) ABSTRACT

The present disclosure provides methods of identifying patients who have partial or total resistance to HIF-2 inhibitors or who develop partial or total resistance to HIF-2 inhibitors after treatment and providing suitable treatment to these patients.

20 Claims, 30 Drawing Sheets

(56) References Cited

OTHER PUBLICATIONS

Wu et al, "Bidirectional modulation of HIF2 activity through chemical ligands", Nature Chemical Biology, vol. 15, pp. 367-376, (2019).
Wu et al, "Structural integration in hypoxia-inducible factors", Nature, vol. 524, pp. 303-308, Aug. 20, 2015.

| | T2WI | ASL | DWI | DCE |
|---|---|---|---|---|
| Imaging plane | Axial | Coronal | Axial | Coronal |
| Acquisition | SShTSE | pCASL with SShTSE | SS-SE-EPI | 3D-T1W-SPGR |
| TR/TE (ms) | 1250/85 | 6000/80 | 1586/64 | 2.4/1.07 |
| FOV (mm²) | 404 x 290 | 400 x 400 | 450 x 320 | 403 x 300 |
| Matrix | 266 x 224 | 128 x 128 | 145 x 108 | 159 x 152 |
| Slice thickness (mm) | 5 | 10 | 5 | 5 |
| Gap (mm) | 1 | - | 1 | 0 |
| Reconstructed voxel size (mm³) | 0.8 x 0.8 x 5 | 1.5 x 1.5 x 10 | 0.7 x 0.7 x 5 | 0.8 x 0.8 x 5 |
| NSA | 1 | 16 | 1 (2 for b=800) | 1 |
| Flip angle (degrees) | 90 | 90 | 90 | 10 |
| Acceleration factor | 3 | - | 3 | 3 |
| Number of slices | 36 | 1 | 50 | 40 |
| Scan duration | 15 sec (x3) | 3 min 30 sec | 2 min 15 sec | 6 min 15 sec |
| Turbo factor | 61 | 72 | - | - |
| Number of dynamic scans | - | - | - | 39 |
| b-values (s/mm²) | - | - | 0, 50, 400, 800 | - |

T2WI, T2-weighted imaging (breath-hold); pCASL, pseudo-continuous arterial spin labeling; DWI, diffusion-weighted imaging (respiratory-triggered); DCE, dynamic contrast-enhanced imaging; TR, repetition time; TE, echo time; FOV, field of view; NSA, number of signal averages; SShTSE, Single-shot turbo spin-echo; SS-SE-EPI, single-shot spin-echo echo planar imaging; 3D-T1W-SPGR, three-dimensional T1-weighted spoiled gradient-echo imaging FIG. 7
(A)
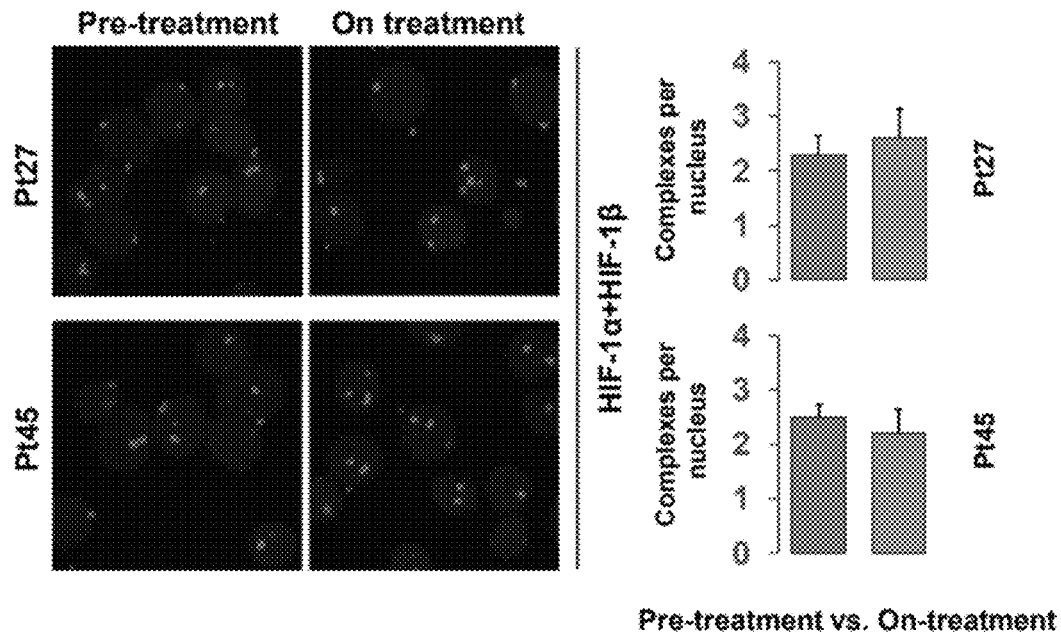
(B)
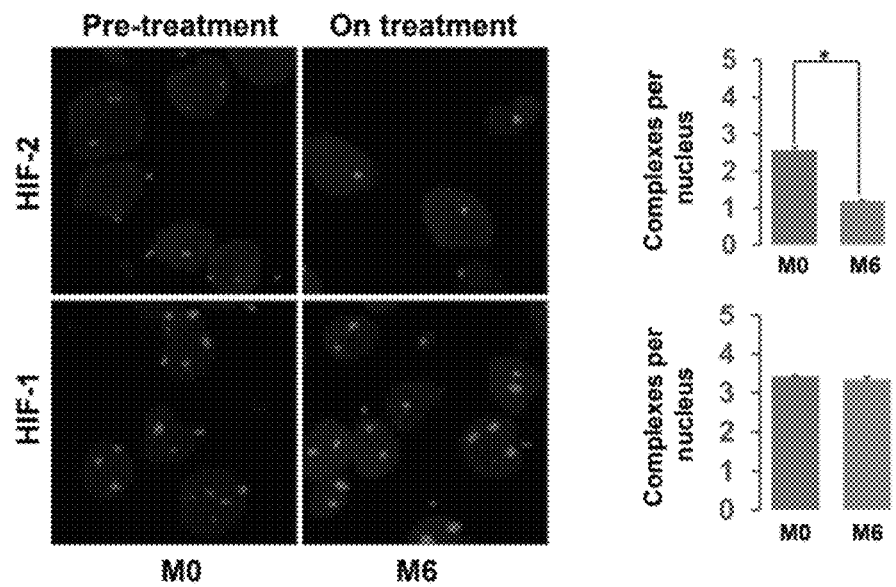

FIG. 8

| Set1 (178 genes) | Set2 (116 genes) | Set3 (48 genes) | Set4 (21 genes) |
|---|---|---|---|
| ADAM12 | IGFBP1 | IGFBP1 | ARHGAP11A |
| ADM | HBB | HBB | C16orf59 |
| ANLN | LEF1 | SERPINE1 | C11orf96 |
| APOBEC3B | SERPINE1 | LEF1 | CCL20 |
| ARHGAP11A | CCL20 | IGFBP3 | CKAP2 |
| ASF1B | PRIMA1 | CCL20 | COL13A1 |
| ASPM | CXCR4 | CXCR4 | CPT1C |
| ATAD2 | SLC43A3 | PRIMA1 | FBXO5 |
| AURKA | C11orf96 | SLC43A3 | GSG2 |
| AURKB | IGFBP3 | C11orf96 | HBB |
| BIRC5 | C16orf59 | LOX | IGFBP1 |
| BLM | TACC3 | RAB27A | LEF1 |
| BRCA1 | MKI67 | SLC6A3 | LOX |
| BUB1 | SLC6A3 | C16orf59 | OIP5 |
| BUB1B | CPT1C | ARHGAP11A | PRIMA1 |
| C10orf10 | RAB42 | RAB42 | PBK11 |
| C16orf59 | RAB27A | COL13A1 | RAB27A |
| C11orf96 | ARHGAP11A | CPT1C | SERPINE1 |
| C15orf48 | PBK11 | C10orf10 | SLC43A3 |
| C16orf74 | COL13A1 | IRS2 | SLC6A3 |
| C17orf53 | MT2A | CCND1 | TACC3 |
| C3orf48 | LOX | CKAP2 | |
| CASC5 | BUB1 | FBXO5 | |
| CCL20 | CENPF | DDIT4 | |
| CCNA2 | CENPE | BUB1 | |
| CCNB1 | C10orf10 | TACC3 | |
| CCNB2 | INHBB | OIP5 | |
| CCND1 | SHCBP1 | APOBEC3B | |
| CDC20 | TPX2 | WDHD1 | |
| CDC45 | CKAP2 | SHCBP1 | |

FIG. 8 (Continued)

| | | | |
|---|---|---|---|
| CDC6 | BIRC5 | SLC39A1 | |
| CDCA3 | ORP5 | GSG2 | |
| CDCA5 | BUB1B | MCM3 | |
| CDCA8 | DLGAP5 | GRPR | |
| CDK1 | DEPDC1 | PRR11 | |
| CENPE | IRS2 | MCM2 | |
| CENPF | CCND1 | KIF15 | |
| CENPH | FBXO5 | STEAP3 | |
| CENPI | KIF20A | ESCO2 | |
| CENPK | RRM2 | CCNA2 | |
| CKAP2 | BLM | NUSAP1 | |
| CKAP2L | CDCA5 | ADAM12 | |
| CKS2 | CDK1 | BUB1B | |
| COL13A1 | KIF15 | ADM | |
| CP5 | APOBEC3B | SLC2A3 | |
| CPT1C | LMNB1 | CASC5 | |
| CXCR4 | ADAM12 | MAD2L1 | |
| DDIT4 | ATAD2 | H2AFZ | |
| DEPDC1 | GSG2 | | |
| DIAPH3 | GRPR | | |
| DLGAP5 | DDIT4 | | |
| DTL | KIF4A | | |
| E2F7 | TTK | | |
| EGFR-AS1 | MYBL2 | | |
| EME1 | NCAPG | | |
| ERCC6L | HMMR | | |
| ESCO2 | WDHD1 | | |
| ESPL1 | PLK4 | | |
| EXO1 | FANCI | | |
| FANCA | KIF23 | | |
| FANCB | PBK | | |
| FANCD2 | FOXM1 | | |
| FANCI | CASC5 | | |
| FBXO43 | MCM3 | | |
| FBXO5 | ESCO2 | | |

FIG. 8 (Continued)

| | | | |
|---|---|---|---|
| FEN1 | NUSAP1 | | |
| FOSL1 | KIAA0101 | | |
| FOXM1 | FXYD1 | | |
| FXYD1 | SLC18A1 | | |
| FXYD3 | DIAPH3 | | |
| GINS1 | ANLN | | |
| GINS2 | MELK | | |
| GINS4 | CCNA2 | | |
| GMNN | MND1 | | |
| GRAMD4 | STEAP3 | | |
| GRPR | ERCC6L | | |
| GSG2 | MAD2L1 | | |
| GTSE1 | UHRF1 | | |
| H2AFZ | CKAP2L | | |
| HBB | MCM10 | | |
| HMMR | RAD51 | | |
| IGFBP1 | AURKA | | |
| IGFBP3 | ADM | | |
| IL27RA | MCM2 | | |
| INHBB | SLC2A3 | | |
| IQGAP3 | CCNB2 | | |
| IRS2 | FBXO43 | | |
| JUN | PRC1 | | |
| KIAA0101 | FXYD3 | | |
| KIF15 | H2AFZ | | |
| KIF18A | PARPBP | | |
| KIF18B | NCAPG2 | | |
| KIF20A | DMC1 | | |
| KIF20B | CENPH | | |
| KIF23 | MASTL | | |
| KIF2C | CCNB1 | | |
| KIF4A | EGFR-AS1 | | |
| KIFC1 | BRCA1 | | |
| KNSTRN | TMEM91 | | |
| KNTC1 | GRAMD4 | | |

FIG. 8 (Continued)

| | | | |
|---|---|---|---|
| LEF1 | C1orf48 | | |
| LGALS3 | JUN | | |
| LGR4 | NUF2 | | |
| LINC00460 | CENPK | | |
| LMNB1 | DTL | | |
| LOX | RACGAP1 | | |
| MAD2L1 | TMEM97 | | |
| MASTL | LGALS3 | | |
| MCM10 | MYH13 | | |
| MCM2 | KIF18A | | |
| MCM3 | CPE | | |
| MCM4 | ASPM | | |
| MCM5 | XRCC2 | | |
| MCM6 | FANCB | | |
| MCM7 | KIFC1 | | |
| MELK | VEGFA | | |
| MKI67 | | | |
| MND1 | | | |
| MT2A | | | |
| MTFR2 | | | |
| MYBL2 | | | |
| MYH13 | | | |
| NCAPG | | | |
| NCAPG2 | | | |
| NUF2 | | | |
| NUSAP1 | | | |
| OIP5 | | | |
| ORC1 | | | |
| PARPBP | | | |
| PBK | | | |
| PLK1 | | | |
| PLK4 | | | |
| PRC1 | | | |
| PRDX1 | | | |
| PRR11 | | | |

FIG. 8 (Continued)

| | | | |
|---|---|---|---|
| PTTG1 | | | |
| RAB27A | | | |
| RAB43 | | | |
| RACGAP1 | | | |
| RAD51 | | | |
| RAD51AP1 | | | |
| RCC1 | | | |
| RRM2 | | | |
| SERPINE1 | | | |
| SHCBP1 | | | |
| SKA3 | | | |
| SLC19A1 | | | |
| SLC2A1 | | | |
| SLC5A3 | | | |
| SLC43A3 | | | |
| SLC6A3 | | | |
| SPC25 | | | |
| STEAP3 | | | |
| SUV39H1 | | | |
| TACC3 | | | |
| TK1 | | | |
| TMEM91 | | | |
| TMEM97 | | | |
| TOP2A | | | |
| TPX2 | | | |
| TRIB3 | | | |
| TROAP | | | |
| TTK | | | |
| UHRF1 | | | |
| VEGFA | | | |
| WDHD1 | | | |
| WDR76 | | | |
| WFDC2 | | | |
| XRCC2 | | | |
| ZWINT | | | |

FIG. 10 Continued
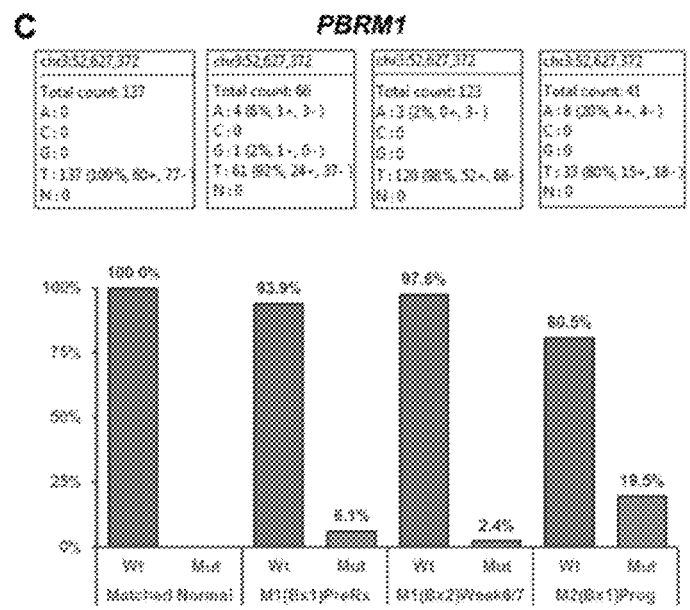
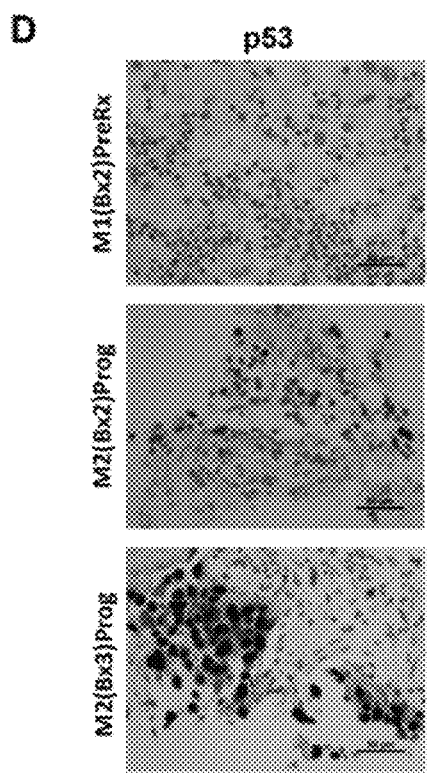

METHODS OF IDENTIFYING AND TREATING PATIENTS WITH HIF-2 INHIBITOR RESISTANCE

PRIORITY

This application claims the benefit of U.S. Provisional Patent Application No. 62/904,268, filed Sep. 23, 2019, which is incorporated by reference herein in its entirety.

GOVERNMENT FUNDING

This invention was made with government support under Grant No. P50CA196516, awarded by the National Institutes of Health. The government has certain rights in the invention.

TECHNICAL FIELD

The present disclosure relates generally to methods to identify patients who have resistance to HIF-2 inhibitors or who develop resistance to HIF-2 inhibitors after treatment.

BACKGROUND

Clear cell renal cell carcinoma (ccRCC) is characterized by inactivation of the tumor suppressor gene, von Hippel-Lindau (VHL), which occurs in the majority of tumors. pVHL functions as the substrate recognition subunit of an E3 ubiquitin ligase complex that targets the a subunit of the heterodimeric hypoxia-inducible factor (HIF) transcription factor for degradation. When VHL is inactivated, HIF-α constitutively accumulates, binds the HIF-1β subunit (also called ARNT), and induces downstream gene expression. Among the 3 known HIF-α subunits, HIF-2α is believed to be the critical ccRCC driver. The HIF-2 complex promotes the expression of over a hundred genes including vascular endothelial growth factor (VEGFA), which binds VEGF receptor-2 (VEGFR2) on endothelial cells, to promote angiogenesis. ccRCC is characterized by high levels of VEGF, and multiple inhibitors of VEGF/VEGFR2 are approved for the treatment of advanced ccRCC.

In addition to VEGF, HIF-2 also stimulates cell cycle progression and maintains stemness, which likely contribute to tumorigenesis. Thus, inhibiting HIF-2 would more broadly target oncogenic pathways; but HIF-2 has traditionally been regarded as undruggable (Koehler, Curr Opin Chem Biol, 2010. 14(3): p. 331-40). However, structural analyses identified a vulnerability in the PAS-B domain of HIF-2α, which paved the way for the development of small molecule inhibitors. These inhibitors induce a conformational change in the PAS-B domain which interferes with the assembly of HIF-2α/HIF-1β heterodimers. These inhibitors led to the development of PT2385 and the highly related tool compound, PT2399. A second-generation HIF-2 inhibitor PT2977, with increased potency and improved pharmacokinetic profile achieved by reduction of phase 2 metabolism is also known. See Xu et al. J. Med. Chem. 62:6876 (2019). Patients, however, can develop resistance to HIF-2 inhibitors. Therefore, methods are needed in the art to identify patients who have resistance to HIF-2 inhibitors or who develop resistance to HIF-2 inhibitors after treatment.

SUMMARY

In an embodiment, a method of treatment is provided comprising determining if cancerous cells of a patient have a HIF2A, HIF1B, or TP53 resistance mutation, and:

(i) if not, then treating the patient with an HIF-2 inhibitor; and
(ii) if so, then treating the patient with one or more therapies other than an HIF-2 inhibitor. Where the patient is treated with an HIF-2 inhibitor, the patient can further be treated with one more additional therapies. The one or more therapies other than an HIF-2 inhibitor comprise chemotherapy (other than HIF-2 inhibitors), cancer immunotherapy, surgical removal of all or part of the cancerous tissue, or radiation therapy. The resistance mutation results in an amino acid substitution in one or more of HIF2α, HIF1β, or p53 proteins. The resistance mutation can result in a G323E amino acid substitution in HIF2α. The resistance mutation can result in a F446L amino substitution in HIF1β. The resistance mutation can result in a R273H amino acid substitution in p53. The HIF-2 inhibitor can be PT2385. The HIF-2 inhibitor can be PT2977. The patient can be a mammal, such as a human. The cancerous cells can be kidney cells, bladder cancer cells, breast cancer cells, colon cancer cells, rectal cancer cells, endometrial cancer cells, leukemia cells, liver cancer cells, lung cancer cells, melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

Another embodiment provides a method of screening of a drug. The method comprises contacting a drug with cancerous cells having one or more HIF2A, HIF1B, or TP53 resistance mutations and determining if the drug detrimentally affects metabolism or growth of the cancerous cells, wherein if the drug detrimentally affects metabolism or growth of the cancerous cells, then is it selected for further testing. The cancerous cells can be kidney cells, bladder cancer cells, breast cancer cells, colon cancer cells, rectal cancer cells, endometrial cancer cells, leukemia cells, liver cancer cells, lung cancer cells, melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

The resistance mutation can result in an amino acid substitution in one or more of HIF2α, HIF1β, or p53 proteins. The resistance mutation can result in a G323E amino acid substitution in HIF2α. The resistance mutation can result in a F446L amino substitution in HIF1β. The resistance mutation can result in a R273H amino acid substitution in p53.

The present disclosure therefore relates to the discovery of methods of identifying patients who have partial or total resistance to HIF-2 inhibitors or those who develop partial or total resistance to HIF-2 inhibitors after treatment.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIG. 1 shows a summary of patients enrolled in phase I companion protocol. Each of the patients has listed age, stage at diagnosis, histology, grade, Von Hippel-Lindau tumor suppressor, E3 ubiquitin protein ligase (VHL) status, number of lines of prior therapies, PT2385 concentration in μg/mL, percent Erythropoietin (EPO) downregulation (2 weeks), percent reticulocyte downregulation (2 weeks), and data on tumor samples.

FIG. 2A shows show integrated mpMRI imaging, pharmacodynamic, and pharmacokinetic analyses for patient 23. FIG. 2B shows show integrated mpMRI imaging, pharmacodynamic, and pharmacokinetic analyses for patient 26. FIG. 2C shows show integrated mpMRI imaging, pharmacodynamic, and pharmacokinetic analyses for patient 27. FIG. 2D shows show integrated mpMRI imaging, pharmacodynamic, and pharmacokinetic analyses for patient 35. FIG. 2E shows show integrated mpMRI imaging, pharmacodynamic, and pharmacokinetic analyses for patient 42. FIG. 2F shows show integrated mpMRI imaging, pharmacodynamic, and pharmacokinetic analyses for patient 44. FIG. 2G shows show integrated mpMRI imaging, pharmacodynamic, and pharmacokinetic analyses for patient 45. Arterial spin labeling (ASL) perfusion and longest diameter (LD) for the same target lesions at indicated time points following PT2385 administration. Erythropoietin is shown over time together along with circulating drug concentrations at trough on day 15. Total weeks on treatment shown at the bottom with the same scale across all patients.

FIG. 4A shows treatment timeline of Pt11 including tumor resections and biopsies. A tumorgraft (PDX model) referred to as XP165 was generated from M0. Subsequently resected or biopsied metastases were designated M1-8. Treatment with the HIF-2 inhibitor (PT2385) was from May 2015-January 2017. FIG. 4B shows computed tomography (CT) images of target and non-target (including biopsied metastasis, #5) at indicated times. FIG. 4C shows WES reads of M4 biopsies (2 cores) showing the HIF2A (EPAS1) 968G>A substitution compared to a matched normal sample from the same patient.

FIG. 4D shows sanger sequencing analyses showing small 968G>A mutant peaks in M4 biopsies compared to reference samples pre-dating PT2385 treatment (M1 and a tumorgraft derived from M0 (T(M0)_TGc1(8133))). FIG. 4E shows proximity ligation assay of HIF-2α/HIF-1β heterodimers in pre-treatment metastasis (M0) and metastasis with resistance mutation (M4) with quantitation. FIG. 4F shows heatmap of HIF-2 signature genes in untreated patient metastasis (M0) as well as tumorgrafts (TG) untreated/vehicle treated (control); followed by treated tumorgrafts and patient tumor biopsy sample with resistance mutation (M4) (under PT drug); and finally a post-trial tumor sample (M7). Line indicates cutoff for the 48 genes downregulated by the HIF-2 inhibitor, but preserved in mutant M4 biopsy sample. n.s., non-statistically significant.

FIG. 5A shows average perfusion in target lesions (Pt number-site) across all patients at baseline, and after 2 weeks (wks), 6-7 weeks, and 16 weeks of PT2385. FIG. 5B shows correlation between maximal percent reduction in ASL perfusion on treatment for patients with available mpMRI and time to progression. Each datapoint represents the average perfusion of all lesions (when more than one lesion assessed by ASL) at the time point exhibiting the maximum reduction in overall ASL perfusion. Datapoint for patient 27 (Pt27) shows an increase in perfusion on treatment. FIG. 5C shows erythropoietin (EPO) levels over time for 3 patients who did not undergo mpMRI. Corresponding drug concentrations at trough (day 15; orange dot). Total weeks on treatment shown by the red bar, standardized across all patients. FIG. 5D shows correlation between drug concentration and the percent decrease in EPO levels. Each data point represents an individual patient. The curve was fit using logarithmic regression ($R2=0.5836$). FIG. 5E shows correlation between relative decrease in EPO levels and relative decrease in reticulocyte count at 2 weeks from baseline. One patient did not have a baseline reticulocyte count measured. The curve was fit using polynomial regression ($R2=0.5798$).

FIG. 6 shows multiparametric magnetic resonance imaging (mpMRI) acquisition parameters.

FIG. 7 panels A-B show PT2385 does not affect HIF-1 complexes. Panel A shows a proximity ligation assay of HIF-1α/HIF-1β complexes of biopsy samples (touchpreps) from Pt27 (iliac mass) and from Pt45 (left adrenal mass) before treatment and on drug. Panel B shows a proximity ligation assay of HIF-2α/H1F-1β heterodimers (top) and HIF-1α/HIF1β heterodimers (bottom) from Pt11. M0, abdominal wall metastasis resected prior to treatment with PT2385; M6, bladder tumor extension during treatment with PT2385. *, $P<0.05$.

FIG. 8 shows genes downregulated by the HIF-2 inhibitor in a tumorgraft line.

DETAILED DESCRIPTION

Methods of Detection

Figure 2A:
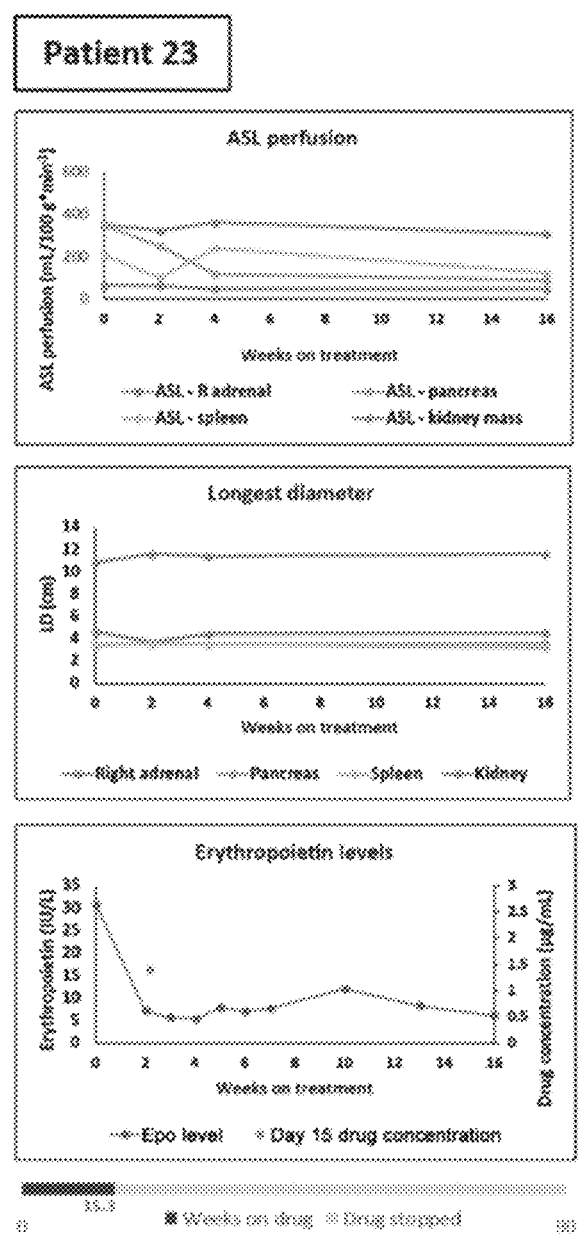
FIGS. 2A-G show integrated mpMRI imaging, pharmacodynamic, and pharmacokinetic analyses in patients participating in phase I trial of PT2385.
Figure 2B:
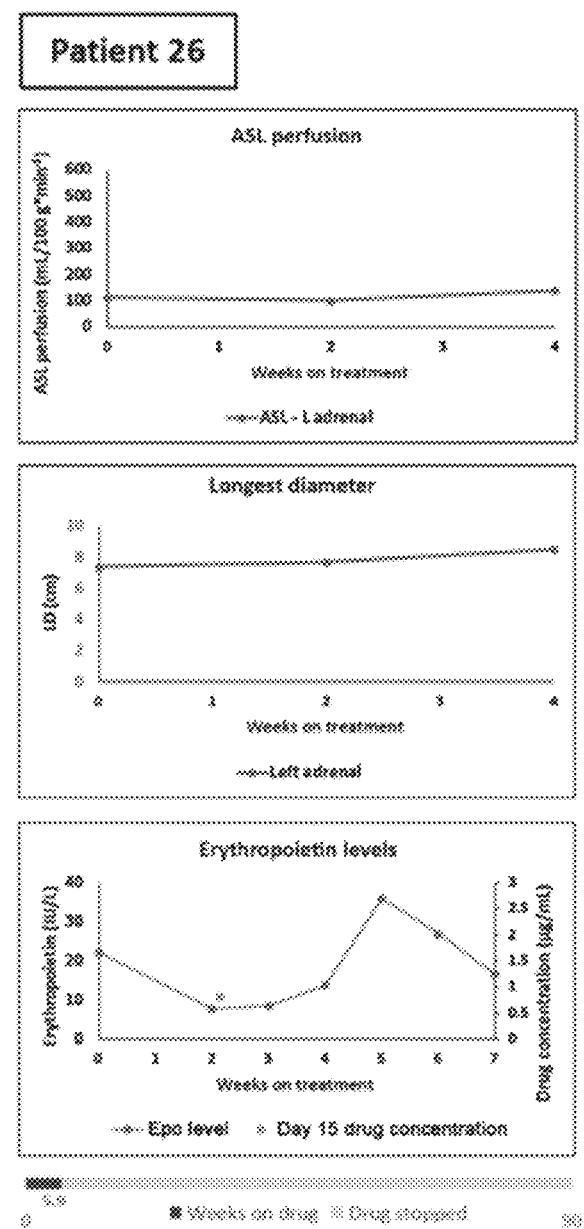

Provided herein are methods of detecting an HIF2A resistance mutation, such as a HIF2A mutation resulting in a G323E mutation, a HIF1B mutation resulting in F446L mutation, and/or a TP53 mutation (e.g., a mutation resulting in a R273H or G245C mutation) in cancerous cells. In one embodiment the cancerous cells are human clear cell renal cell carcinoma cells, but any cancer cells or cancer patients can be screened. Detection of one or more HIF2A, HIF1B, or TP53 resistance mutations can indicate resistance to HIF-2 inhibitors such as PT2385 or PT2977 in a patient. Therefore, a method is provided for detecting whether a patient has a HIF2A, HIF1B, or a TP53 mutation that results in a resistance of cells to treatment with an HIF-2 inhibitor such as PT2385 or PT2977.

A HIF2A mutation resulting in a G323E mutation means that the glycine (G) at position 323 of the HIF2A protein is substituted with glutamic acid (E). A TP53 mutation resulting in a R273H mutation means that the arginine (R) at position 273 of the TP53 protein is substituted with histidine (H). A TP53 a mutation resulting in a G245C mutation means that the glycine (G) at position 245 of the p53 protein is substituted with cysteine (C). A HIF1B mutation resulting in a F446L mutation means that the phenylalanine (F) at position 323 of the HIF1β protein is substituted with leucine (L) (see, Chen et al., Nature, 539:112 (2016)).

If a patient has a HIF2A, HIF1B, or a TP53 mutation in cancerous cells that results in a resistance of the cancerous cells to treatment with an HIF-2 inhibitor such as PT2385 or PT2977, then the patient can be labeled as a non-responder to HIF-2 inhibitors such as PT2385 or PT2977. If a patient does not have a HIF2A, HIF1B, or a TP53 mutation in cancerous cells that results in a resistance of cells to treatment with an HIF-2 inhibitor such as PT2385 or PT2977, then the patient can be labeled as a responder to HIF-2 inhibitors such as PT2385 or PT2977. If a patient is a responder, then they can be treated with one or more HIF-2 inhibitors, optionally in combination with one or more other cancer treatments.

Multiple methods exist to detect HIF2A, HIF1B, or TP53 resistance mutations. These methods can be performed on formalin-fixed paraffin-embedded (FFPE) cancer tissues, frozen cancer tissues, fresh cancer tissues, cancerous cells, or any other suitable biological sample.

Direct dideoxynucleotide (Sanger) sequencing is a method for determining the nucleotide sequence of DNA. Direct sequencing can identify HIF2A, HIF1B, or TP53 resistance mutations. Mutations can also be detected using, for example, polymerase chain reaction (PCR). PCR steps amplify DNA regions of interest and multiplex single-base primer extension with dideoxynucleotides. Extension products can then be analyzed by, for example, mass spectrometry, which can distinguish different bases according to their mass-to-charge (m/z) ratio (Sequenom Mass Spectrometry system) or by capillary electrophoresis, which distinguishes bases by size and by the color of fluorescently labeled nucleotides (Applied Biosystems SNaPshot system). See Fumagalli et al., *BMC Cancer,* 10:101 (2010).

Direct dideoxynucleotide (Sanger) sequencing is a method for determining the nucleotide sequence of DNA. Direct sequencing can identify HIF2A, HIF1B, or TP53 resistance mutations. Mutations can also be detected using, for example, polymerase chain reaction (PCR). PCR steps amplify DNA regions of interest and multiplex single-base primer extension with dideoxynucleotides. Extension products can then be analyzed by, for example, mass spectrometry, which can distinguish different bases according to their mass-to-charge (m/z) ratio (Sequenom Mass Spectrometry system) or by capillary electrophoresis, which distinguishes bases by size and by the color of fluorescently labeled nucleotides (Applied Biosystems SNaPshot system). See Fumagalli et al., *BMC Cancer,* 10:101 (2010).

Methods of Treatment

In an embodiment, a method of treatment is provided. The method comprises determining if cancerous cells of a patient have a HIF2A, HIF1B, or TP53 resistance mutation and if not, then treating the patient with an HIF-2 inhibitor. The HIF-2 inhibitor can be, for example, PT2385 or PT2977. PT2977 and PT2385 are orally active, small molecule inhibitors of hypoxia inducible factor (HIF)-2α that allosterically bind to HIF-α, preventing HIF-α heterodimerization and subsequent DNA binding, and thereby decrease transcription and expression of HIF-α downstream target genes in tumor cells.

PT2385 (Chemical formula: $C_{17}H_{12}F_3NO_4S$) has a $K_i$ of less than 50 nM. PT2385 is inactive for HIF-1α. PT2977 (chemical formula: $C_{17}H_{12}F_3NO_4S$) has an $IC_{50}$ of 9 nM.

In some embodiments, PT2385 allosterically binds to HIF-2α, preventing HIF-2α heterodimerization and subsequent DNA binding. PT2385 binding to HIF-2α thereby decreases transcription and expression of HIF-2α downstream target genes, many of which regulate tumor cell growth and survival. Similarly, in some embodiments, PT2977 binds to and blocks the function of HIF-2α, preventing HIF-2α heterodimerization and subsequent DNA binding. PT2977 binding to HIF-2α thereby decreases transcription and expression of HIF-2α downstream target genes, many of which regulate hypoxic signaling. Both PT2385 and PT2977 inhibit cell growth, survival, and proliferation of HIF-2α-expression tumor cells.

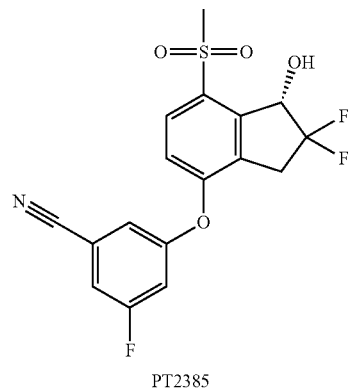

PT2385

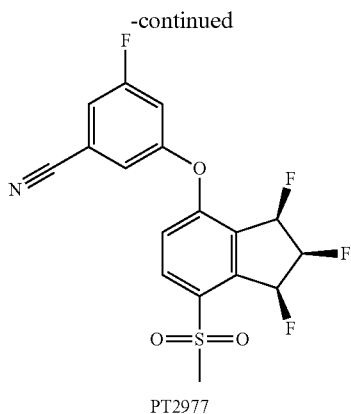

PT2977

In an embodiment a patient is tested for resistance to HIF-2 inhibitors prior to any treatment with HIF-2 inhibitors. In an embodiment, a patient is tested for resistance to HIF-2 inhibitors after treatment with HIF-2 inhibitors (e.g., after about 1 month, 3 months, 6 months, 9 months, 1 year or more after initial treatment).

HIF-2 inhibitors such as PT2977 and PT2385 can be administered orally once a week, every other day, every day, twice a day, three times a day, four times a day, five times a day or more at about 25, 50, 75, 100, 200, 300, 400, 500, 600, 700, 800, 900, 1,000, 1,100, 1,200, 1,300, 1,400, 1,500, 1,600, 1,700, 1,800, 1,900, 2,000 mg or more (or any range between about 25, and 2,000 mg). See e.g., Jonasch et al., *Annals of Oncology*, 30, Suppl. 5, October 2019. Treatment with HIF-2 inhibitors can be alone or in combination with immunotherapy, for example, checkpoint inhibitors such as nivolumab, ipilimumab, pembrolizumab, or atezolizumab. HIF-2 inhibitors can also be administered in combination with any of one or more other cancer treatments as described below.

In an embodiment, where the cancerous cells of a patient do have a HIF2A, HIF1B, or TP53 resistance mutation, then the patient can be treated with other treatment methods. Other methods of treatment can include, for example, chemotherapy, cancer immunotherapy (i.e. the artificial stimulation of the immune system to treat cancer, improving on the immune system's natural ability to fight the disease). Types of cancer immunotherapy include, for example, monoclonal antibodies and tumor-agnostic treatments (e.g., checkpoint inhibitors), oncolytic virus therapy, T-cell therapy, and cancer vaccines. Additional treatments include, for example, surgical removal of all or part of the cancerous tissue, radiation therapy, or targeted therapy. Chemotherapy drug treatments for cancer such as clear cell renal cell carcinoma can include, for example, sunitinib, temsirolimus, axitinib, cabozantinib, pazopanib, and sorafenib. Sunitinib targets multiple receptor tyrosine kinases (RTKs). Temsirolimus, axitinib, cabozantinib, pazopanib, and sorafenib are other kinase inhibitors that can be used. Other treatments for cancer, including clear cell renal cell carcinoma, include for example, bevacizumab, which is classified as both a chemotherapy drug and a targeted therapy drug. Bevacizumab is a monoclonal antibody that functions as an angiogenesis inhibitor. Cancer, such as clear cell renal cell carcinoma can also be treated by IL-2, also called aldesleukin, which is an antineoplastic (anticancer) biologic response modifier. It is noted that any of these treatments can be used in combination with one or more HIF-2 inhibitors for patients lacking HIF2A, HIF1B, or TP53 resistance mutations.

In an embodiment the patient is a mammal such as a human. The tumor cells can be present in clear cell renal cell carcinoma cells or any other type of cell (including non-cancerous cells). PT2385 or PT2977 can reduce HIF-2 in both tumor and non-tumor tissues.

In an embodiment the cancer cells are kidney cancer cells such as clear cell kidney cells, papillary kidney cells, medullary collecting duct kidney cells, chromophobe kidney cells, oncocytoma kidney cells, or angiomyolipoma kidney cells. In an embodiment the cancerous cells are bladder cancer cells, breast cancer cells, colon cancer cells, rectal cancer cells, endometrial cancer cells, leukemia cells, liver cancer cells, lung cancer cells (e.g., non-small cell lung cancer cells, small cell lung cancer cells), melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

In an embodiment, a patient has kidney cancer such as clear cell kidney cancer, urothelial carcinoma, sarcoma of the kidney, Wilms tumor, or kidney lymphoma. In an embodiment a patient has bladder cancer, breast cancer, colon cancer, rectal cancer, endometrial cancer, leukemia, liver cancer, lung cancer (e.g., non-small cell lung cancer or small cell lung cancer), melanoma, non-Hodgkin lymphoma, pancreatic cancer, prostate cancer, thyroid cancer, parathyroid cancer, neuroblastoma, lymphoma, adrenocortical cancer, sarcoma, bile duct cancer, brain cancer, bone cancer, gastrointestinal cancer, cardiac cancer, cervical cancer, chronic myeloproliferative neoplasm, esophageal cancer, head and neck cancer, retinoblastoma, gall bladder cancer, testicular cancer, ovarian cancer, or laryngeal cancer.

Methods of Screening

An embodiment provides methods of screening of a drug for activity in killing or slowing the growth or metabolism of cancerous cells. Methods can comprise contacting a test drug with cancerous cells having a HIF2A, HIF1B, or TP53 resistance mutation and determining if the drug detrimentally affects metabolism or growth of the cancer cell. If the candidate drug detrimentally affects metabolism or growth of the cancerous cells, then it can be selected for further testing.

In an embodiment the cancer cells are kidney cancer cells such as clear cell kidney cells, papillary kidney cells, medullary collecting duct kidney cells, chromophobe kidney cells, oncocytoma kidney cells, or angiomyolipoma kidney cells. In an embodiment the cancerous cells are bladder cancer cells, breast cancer cells, colon cancer cells, rectal cancer cells, endometrial cancer cells, leukemia cells, liver cancer cells, lung cancer cells (e.g., non-small cell lung cancer cells, small cell lung cancer cells), melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

Cancerous cells having a HIF2A, HIF1B, or TP53 resistance mutation as described herein can be cultured in any suitable media. The cell culture media can be replaced (such as when passing the cells) or supplemented during culturing. The replacement media can be the same formulation or have a different formulation that the prior media. Other media components can be supplemented to the media during culturing, which can result in a change in the media formulation. Any number of cell characteristics can be measured or detected before, during, or after contact with a test drug. For example, cell number, cell morphology, cell metabolism, or cell growth can be measured or analyzed. The cells can be counted manually counted or counted by an automated system. The cells can be analyzed by, for example, flow cytometry or spectrophotometry. The cells can be stained with, for example, dye, conjugated antibodies, fluorophores, or fluorochrome conjugated antibodies. A test drug can be an existing drug or candidate drug for the treatment of cancer. A test drug can be any compound, small molecule, protein, antibody, or other agent for which data relating to cancer cell treatment is desired. Test drugs identified by the screening methods can be used, for example, to reduce the growth of cancerous tissues or tumors in a subject, kill cancerous tissues or cells in a subject, or arrest the increase in cell number, cell mass, or both, in cancerous tissues or cells in a subject.

A test drug can be added to the culture medium in which cancerous cells having a HIF2A, HIF1B, or TP53 resistance mutation are present. A test drug can be added to the culture medium at varying concentrations and/or varying times after the cells are cultured.

Half maximal inhibitory concentration, or $IC_{50}$, is a measurement representing the halfway point in which a test drug produces complete inhibition of a biological or biochemical function. This information can be obtained based on pharmacological data in reference to a dose-response curve. As the dosage of an inhibitory compound is increased, the biological function it affects decreases. $IC_{50}$ may be used as a measurement of antagonist, or inhibitory drug potency, as well as a quantification of the toxicological effects of inhibitory compounds. The $IC_{50}$ can be calculated using, for example, Graph Pad Prism.

In an embodiment a test drug can inhibit HIF-2 with an $IC_{50}$ of from about 100 nM to about 10 μM or from about 250 nM to about 5 μM, or from about 500 nM to about 1 μM. In an embodiment HIF-2 inhibition can be determined by measuring reduction in erythropoietin levels (a pharmacodynamic marker).

A test drug that is suitable for cancer treatment can have a lower $IC_{50}$ than the $IC_{50}$ of a control. A test drug that is suitable for cancer treatment can be determined to have a lower $IC_{50}$ than the $IC_{50}$ of other drugs tested. A test drug that is suitable for cancer treatment can show efficacy against cancer cells at $IC_{50}$ values of less than about 500, 250, 100, 75, 50, 10, 5, or 1 μM. A test drug that is suitable for cancer treatment can show efficacy against cancer cells at $IC_{50}$ values less than about of 1000, 750, 500, 250, 200, 150, 100, 50, 25, 10, 5, or 1 nM.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Methods and Methods
Study Design and Participants

A companion study involving a subset of patients in the phase I clinical trial "Phase I, Multiple-Dose, Dose-Escalation Trial of PT2385 Tablets, a HIF-2α Inhibitor, in Patients with Advanced Clear Cell Renal Cell Carcinoma (NCT02293980)" was conducted. All patients in this companion study were enrolled in the Phase I trial, and all were treated at the recommended phase II dose or above. The study involved several interventions, including contrast-enhanced magnetic resonance imaging (MRI), which required a eGFR ≥30 mL/min/1.73 m2 and at least one candidate intra-abdominal, intra-thoracic, or osseous lesion >2.5 cm. Subjects who had a contraindication to MRI could still participate in the blood collection and optional tumor biopsy portions of this study. Patient identification numbers are chronological and were those assigned for the phase I trial. Descriptive data is presented and includes weeks on treatment as well as progression free survival (PFS), which may differ depending upon when drug was stopped.

Procedures

Multiparametric MRI (mpMRI) was performed and blood samples were collected during screening, on treatment (at 2 weeks, 6-7 weeks, and 16 weeks), and at progression. Optional core tumor biopsies were performed during screening, on treatment (at weeks 6-7), and at progression. Additional core biopsies could be obtained from a responding or progressing lesion at one additional time point while the patient was on treatment. Erythropoietin (EPO) levels and plasma concentration of PT2385 were measured as part of the phase I trial.

MR Imaging Protocol and Analyses

All exams were performed on a 3T MRI scanner (Phillips, Best, Netherlands) using a phased-array surface coil. Coronal and axial T2-weighted imaging, axial diffusion weighted imaging (DWI), and coronal dynamic contrast enhanced (DCE) acquisitions were obtained through the abdomen (FIG. 6). DCE MRI was performed with a three-dimensional (3D) T1-weighted (T1W) spoiled gradient-echo (SPGR) acquisition before, during, and after the intravenous administration of 0.1 mmol/kilogram of gadobutrol (Gadavist; Bayer Healthcare Pharmaceuticals, Wayne, N.J.) at a rate of 2 mL/sec followed by a 20 mL saline flush at 2 mL/sec. Images were obtained for a total of 6 minutes and 15 seconds with a 5 second temporal resolution. Three dynamic phases were acquired during breath-hold intervals with 15-second free-breathing cycles. To generate a T1 map, 3 additional coronal 3D T1W SPGR acquisitions were obtained prior to the administration of contrast using the same acquisition parameters as those of the DCE MRI acquisition except for flip angles of 10o, 5o, and 2o, respectively.

2D arterial spin labelled (ASL) MRI was acquired prior to administration of contrast via pseudo-continuous labeling of the abdominal aorta (FIG. 6). See Robson et al., *Magn Reson Med,* 2009. ASL images were prescribed in the axial or coronal plane to cover the center of each target lesion.

mpMRI acquisition parameters for ASL, DCE, and DWI are presented in FIG. 6. DCE images were processed using a commercial software (VersaVue, iCAD Inc., Nashua, N.H.) to generate quantitative maps of $K^{trans}$ and $K_{ep}$ from the extended Tofts model. ASL perfusion difference and quantitative perfusion maps were generated using Matlab (The MathWorks Inc., Natick, Mass.). Apparent Diffusion Coefficient maps ($mm^2/s \times 10^{-3}$) were generated using a mono-exponential model.

All MRI acquisitions were reviewed on an open-source Picture Archiving and Communication System workstation (OsiriX, Pixmeo, Bernex, Switzerland). Regions of interest (ROIs) were drawn on the pre-treatment mpMRI. Subsequent mpMRIs were analyzed by drawing ROIs in the same lesions using the baseline mpMRI as the reference for comparison. The radiologist was blinded to clinical data but unblinded to patient study ID. On the quantitative ASL perfusion maps, whole lesion ROIs were drawn to outline the periphery of the lesion, avoiding the contour to minimize partial volume effects, to determine the mean perfusion level of the lesion in millimeters per minute per 100 g of tissue (mL/min/100 g). Similar ROIs of the entire lesion were drawn on the DCE quantitative $K^{trans}$ ($min^{-1}$) and $K_{ep}$ ($min^{-1}$) maps, on a slice location that best matched the position of the ASL acquisition when feasible. On the ADC maps, a whole lesion ROI was drawn on a single image that included the center of each target lesion. Data on DCE and DWI were not informative and are not included.

Proximity Ligation Assay (PLA)

Proximity ligation assays were performed. Mouse anti-HIF-1α (NB100-105, Novus), mouse anti-HIF-2α (sc-46691X, Santa Cruz) and rabbit anti-ARNT/HIF-1β (A302-765A, Bethyl) were used. Primary antibodies were concentrated and buffers were exchanged using a Vivaspin 500 Centrifugal Concentrator (VS0131, Fisher Scientific). Antibodies were diluted to 1 mg/ml in phosphate buffered saline. Primary antibody conjugation was done with a Duolink In situ Probemaker MINUS/PLUS kit (DUO92010 & DUO92009, Sigma-Aldrich). Briefly, 2 µl of conjugation buffer was added to 20 µl of the antibody (1 mg/ml), mixed gently, transferred to one vial of lyophilized oligonucleotide (PLUS or MINUS), and incubated at room temperature overnight. 2 µl of stop reagent was then added to the reaction and incubated at room temperature for 30 min. 24 µl of storage solution was added and the conjugate was stored at 4° C. Tumor tissue was blocked with phosphate buffered saline-Triton (0.1% Triton X-100)+1% BSA for 30 min after antigen retrieval. Conjugated HIF-1α-MINUS, HIF-2α-MINUS and HIF-1β-PLUS were diluted in blocking buffer containing 1× assay reagent at a dilution of 1:50, 1:50, and 1:200, respectively. The antibodies were allowed to sit for 20 min at room temperature before they were added to each sample. Slides were incubated in a humidity chamber overnight at 4° C. Duolink In situ Detection Reagents FarRed (DUO92013-30RXN, Sigma-Aldrich) were used for signal detection. Briefly, slides were washed with wash buffer A (Cat. No. DUO82047, Sigma-Aldrich), a ligation solution containing ligase at a 1:40 was added, and slides were incubated in a pre-heated humidity chamber for 30 min at 37° C. After washing in buffer A with gentle agitation, amplification solution containing the polymerase was added at a 1:80 dilution, and slides were then incubated in a pre-heated humidity chamber for 100 min at 37° C. After washing in buffer B (Cat. No. DUO82048, Sigma-Aldrich) and then 0.01× buffer B, slides were dried at room temperature in the dark and mounted with a cover slip using a minimal volume of Duolink In situ Mounting Medium with DAPI (DU082040, Sigma-Aldrich). After approximately 15 min, slides were analyzed by confocal microscopy (Nikon) using a 63× objective. Image analysis was done with the ImageJ 1.48V program, and performed blinded to the sample IDs. Pictures of three fields for each sample were used. At least 20 cells of each sample were counted. Pt27 samples were derived from touchpreps of an iliac mass biopsy pre-treatment and then a biopsy of this same mass at week 6/7 on-treatment. Pt35 samples were derived from touchpreps of a liver tumor biopsy pre-treatment and then a biopsy of this same mass at week 6/7 on-treatment. Pt45 samples were derived from touchpreps of a left adrenal mass biopsy pre-treatment and then a biopsy of this same mass at week 6/7 on-treatment.

Whole Exome Sequencing (WES) and Mutation Calling

WES was performed and DNA libraries were prepared using Integrated DNA Technologies xGen Lockdown Panel v1.0. Libraries were then sequenced at ≥100× coverage using Illumina's HiSeq 4000 with 150 bp pair-end reads. The Quantitative Biomedical Research Center (QBRC) mutation calling pipeline was used for somatic mutation calling. In short, exome-seq reads were aligned to the human reference genome (Hg38) by BWA-MEM. Picard was used to add read group information and sambamba was used to mark PCR duplicates. The Genome Analysis Toolkit was used to perform base quality score recalibration and local realignment around insertion/deletions (indels). MuTect, VarScan, Shimmer, SpeedSeq, Manta, and Strelka2 were used to call single nucleotide polymorphisms (SNPs) and indels. A mutation that was repeatedly called by any two of these software programs was retained. Annovar was used to annotate SNPs and indels, as well as protein sequence changes. All SNPs and indels were combined and only kept if there were at least 7 total reads in the normal sample (wild-type and variant) and at least 3 variant reads in the tumor sample. Intronic, untranslated regions, and intergenic mutations were filtered out. Missense mutations predicted as benign by both PolyPhen-2 and Sorting Intolerant from Tolerant (SIFT), which have a <5% chance to induce functional changes at the protein level, were filtered out. Somatic mutations were annotated according to the variant allele frequencies in the normal (<5%) and tumor (>5% and at least two times larger than the variant allele frequency in the normal sample) samples. These studies were complemented through direct visualization of the mutated reads using the Integrated Genomics Viewer (IGV; Broad Institute). Color of the mutation depends upon the type of substitution.

RNA-Seq and Analyses mRNA was extracted from total RNA from flash frozen tumor tissue using NEBNext® Poly(A) mRNA Magnetic Isolation Module Kits from New England BioLabs and library preparation was performed using Illumina's NEBNext® Ultra™ RNA Library Prep Kit. Sequencing was performed at Admera Health Precision Medicine and Molecular Diagnostics Lab using Illumina's HiSeq4000 with average sequencing depth of 40M reads and 150 bp pair-end reads. FastQC (https://www.bioinformatics.babraham.ac.uk/projects/fastqc/) was applied to conduct quality control procedures, with the parameters '--extract --threads 48 -q'. RNA-Seq reads were aligned to the human reference genome GRCh38 (hg38) using STAR with the parameters '--runThreadN 48 --outSAMtype BAM Unsorted --outReandsUnmapped Fastx'. FeatureCounts with parameters '--primary -O -t exon -g transcript_id -s 0 -T 48 --largestOverlap --minOverlap 3 --ignoreDup -p -P -B -C' was then used to measure gene expression levels. The human genome annotation file employed by FeatureCounts was downloaded from UCSC table browser under the RefSeq Gene track. Downstream analyses were performed in an R computing environment. Reads Per Kilobase Million (RPKM) values were calculated from gene read counts. RPKM values were then Log 2-transformed and quantile normalized.

Gene signature enrichment analysis was carried out using the single sample gene set enrichment analysis (ssGSEA) method given a set of signature genes (e.g. HIF-2 target signature). Specifically, ssGSEA analysis was performed using the R Gene Set Variation Analysis (GSVA) package by calling the gsva function with parameter method="ssgsea" and rnaseq=T.

Statistical Analyses

For mpMRI, planned analyses were mostly descriptive. Continuous variables were summarized by mean, standard deviation and 95% confidence interval, and categorical variables were summarized by frequency and percentage. Intra-patient changes in tumor perfusion (by ASL), $K^{trans}$ (by DCE), and ADC (by DWI), were estimated together with their 95% confidence intervals. Median and 95% CI were used to report the response to PT2385 in terms of (i) RECIST 1.1, (ii) 10% reduction in sum of the longest one-dimensional diameters (SLD), (iii) change in $K^{trans}$, and (iv) ADC. Significance of ASL perfusion changes at two weeks of PT2385 treatment was determined using a linear mixed model.

A logarithmic regression was used to fit the curve of EPO with trough PT2385 levels, while polynomial regression was used to fit the curve of EPO with reticulocytes. For PLA analyses, the Student t-test was used to analyze for significant differences by patient in the number of HIF-1 and HIF-2 complexes between pre-treatment and on-treatment tissue samples. Gene set enrichment analysis for HIF-2 target genes, was completed using the GSVA package with the ssGSEA method. A mixed model was used to determine if the expression estimates obtained were significantly different for pre-treatment versus on-treatment patient biopsies from sensitive patients, using a compound symmetric covariance structure to account for correlation of estimates from the same patient. Heatmaps were created to visualize the expression of individual genes of the HIF-2 target gene signature.

Results

Figure 1:
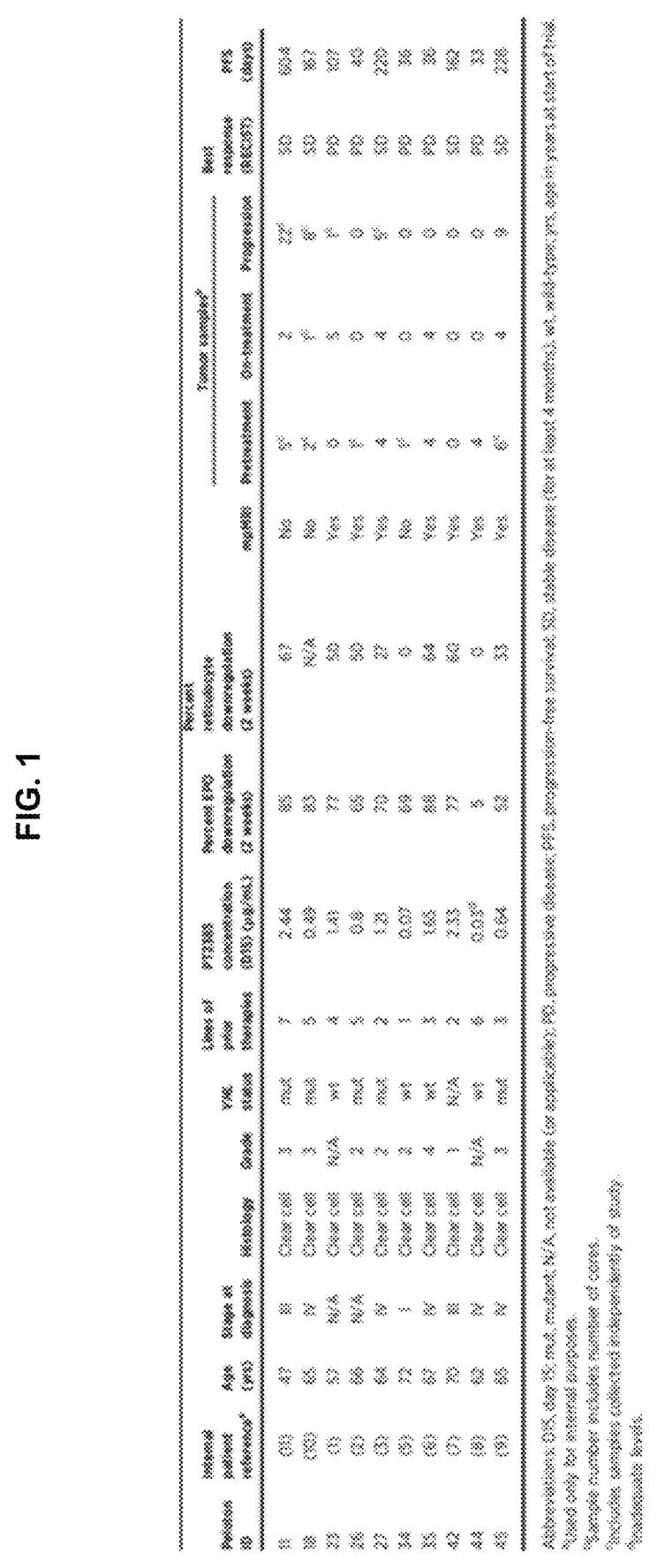

To obtain insight into the mechanism of PT2385 action against ccRCC in humans, an approved protocol (UTSW STU 062015-063) was implemented enabling translational studies on patients participating in the PT2385 phase I trial (NCT02293980). Among 51 patients from 6 institutions in the phase I trial, 26 patients enrolled in the dose-escalation phase and 25 in the dose-expansion. Eleven patients enrolled in the study at the recommended phase II dose level or above, including 10 that participated in this companion study (FIG. 1). The patient population was extensively pre-treated with a median number of 3.5 prior lines of therapy. Among these patients, 5 had stable disease for at least 4 months (median 6.9 months) and 5 had progressive disease. VHL was mutated in tumors from 5 out of 9 patients for whom samples were available and VHL mutations were enriched among patients with stable disease. However, a VHL mutation was also found in a patient with progressive disease (FIG. 1).

Multiparametric MRI Analyses

Figure 2C:
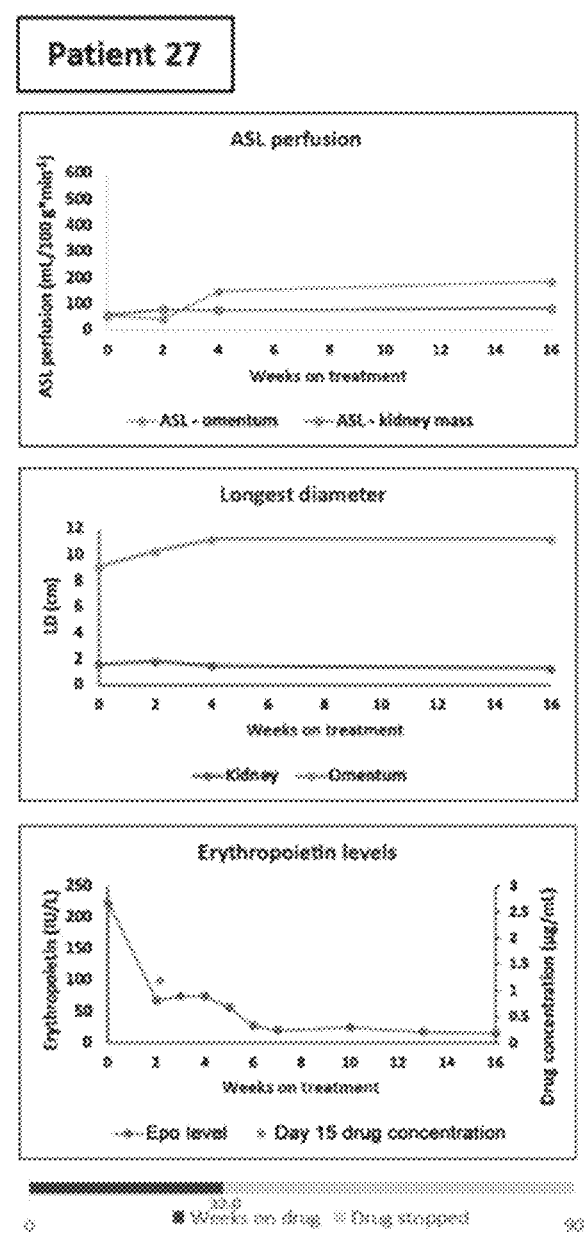
Figure 2D:
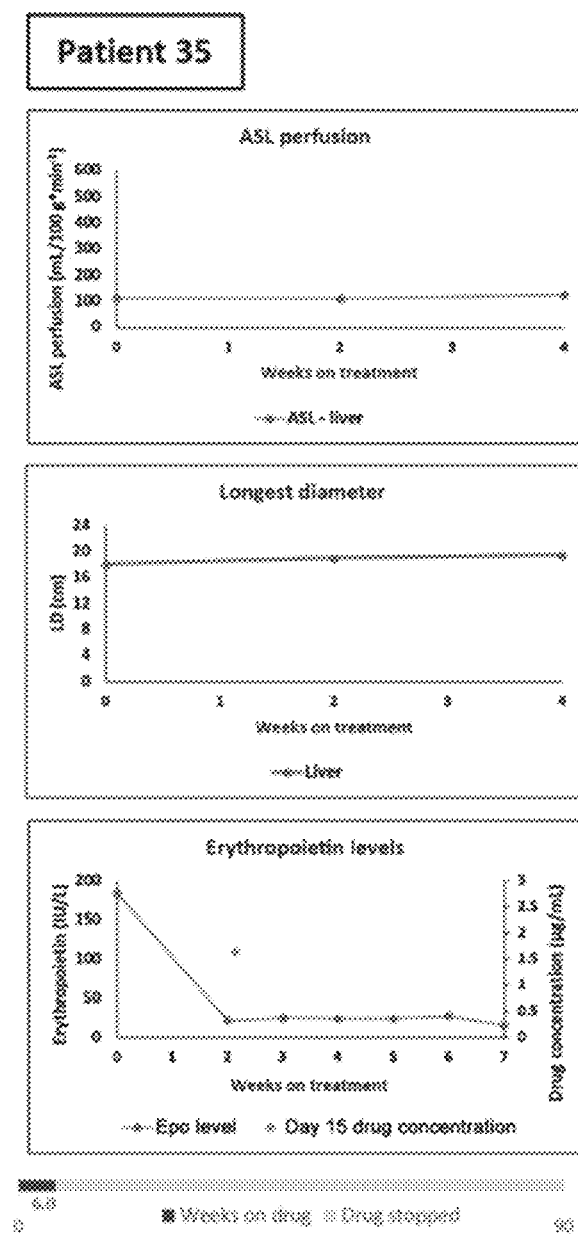
Figure 2E:
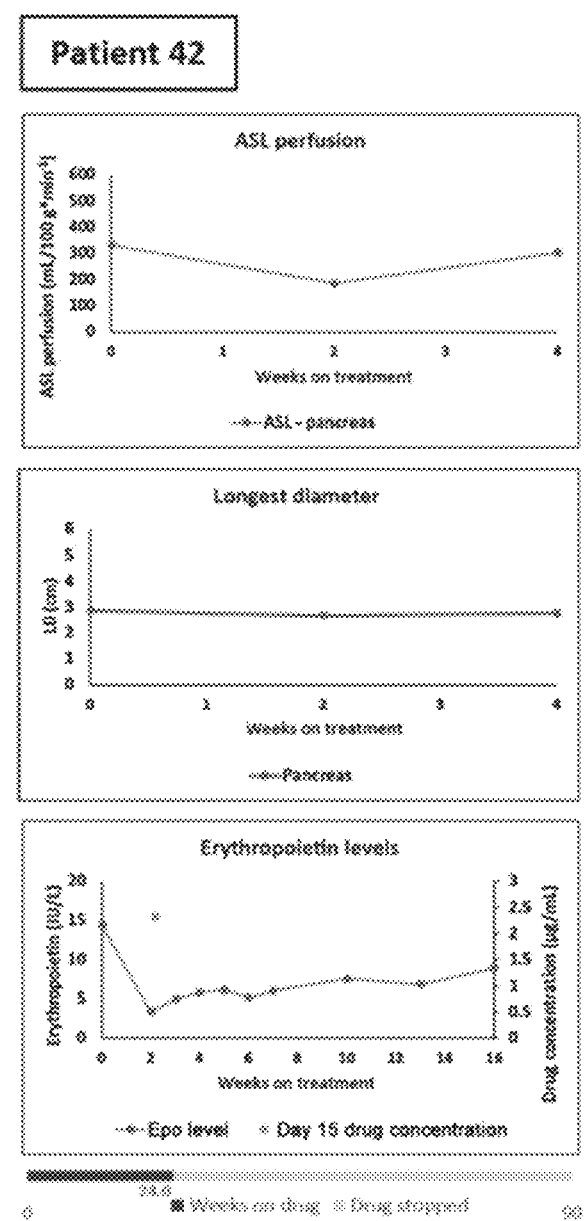
Figure 5A:
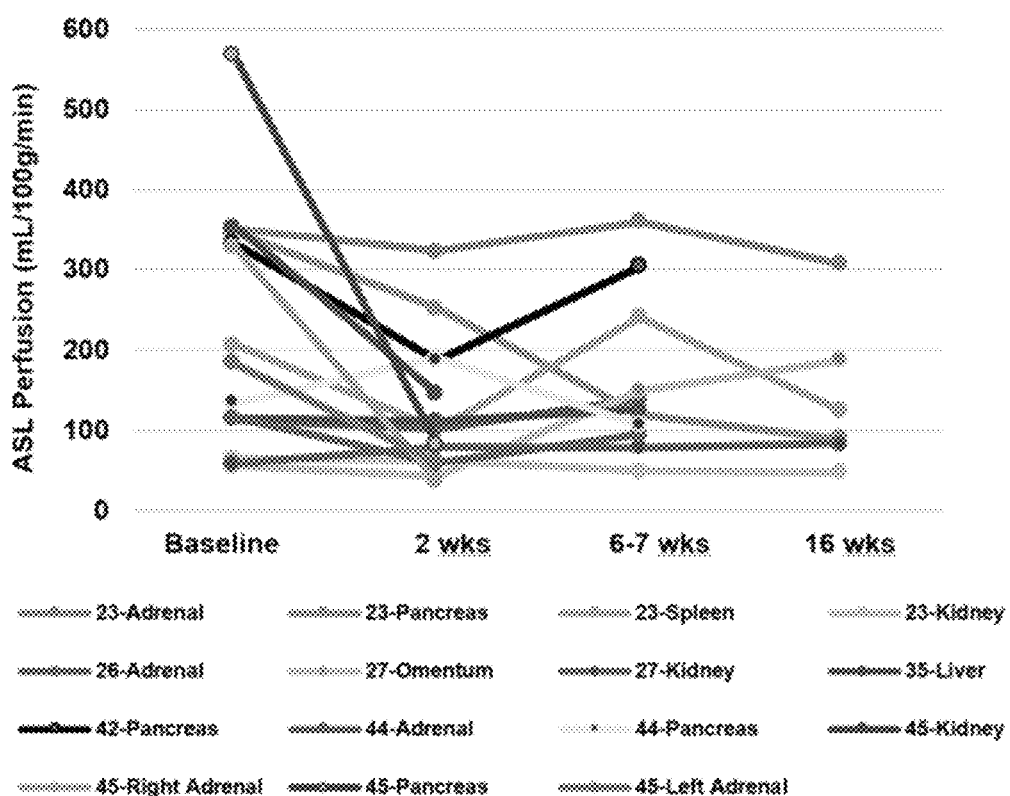
FIG. 5A-E shows pharmacodynamic analyses and illustrative mpMRI studies.
Figure 5B:
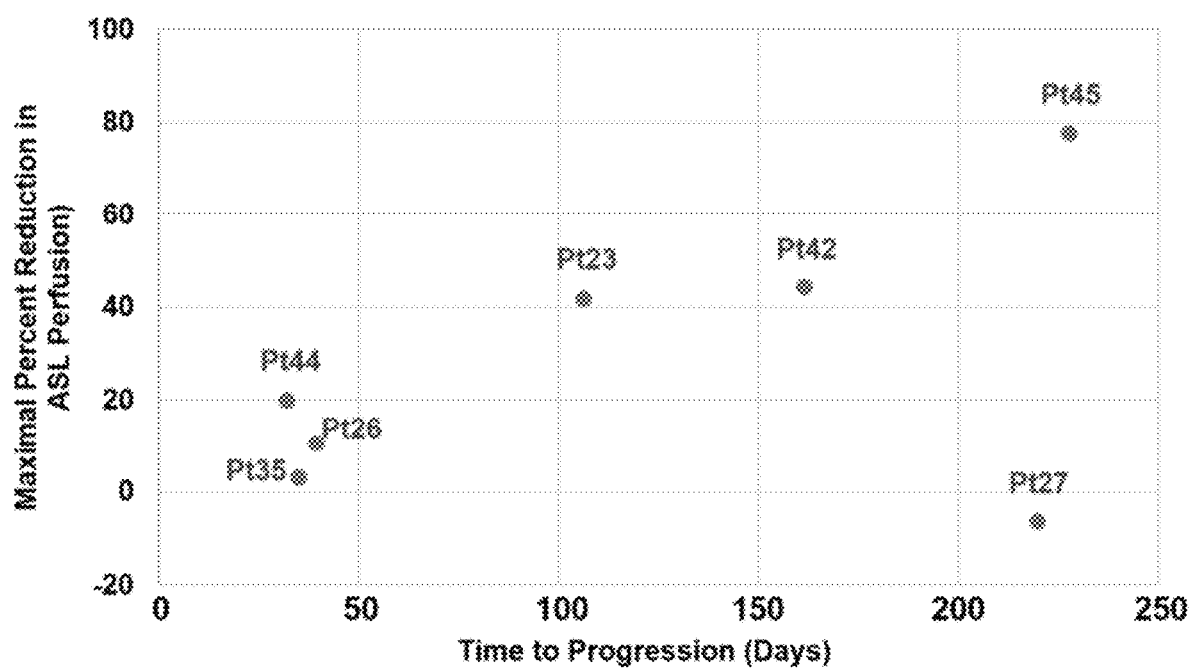

The effects of PT2385 with mpMRI were explored. ASL MRI was used to estimate tumor perfusion, which has been previously employed to evaluate antiangiogenic therapy (FIG. 6). See Bharwani et al., *Br J Cancer,* 2014; de Bazelaire, et al., *Clin Cancer Res,* 2008; Flaherty, et al., *Cancer Biol Ther,* 2008; Hahn, et al., *J Clin Oncol,* 2008; & Schor-Bardach, et al., *Radiology,* 2009. Seven patients underwent mpMRI. ASL perfusion at sites of metastases were measured at baseline and following PT2385 initiation (FIG. 2A-G). ASL changes with changes in tumor size were correlated. At 2 weeks, ASL perfusion decreased by 29% on average, but this was largely driven by changes in one patient (Pt45; FIG. 2G; FIG. 5A). Maximal changes in ASL with time to progression were correlated, and with one exception (Pt27), greater reductions in ASL were associated with longer time to progression (FIG. 5B).

Functional HIF-2 Inhibition in Non-Tumor Tissues by PT2385

Figure 5C:
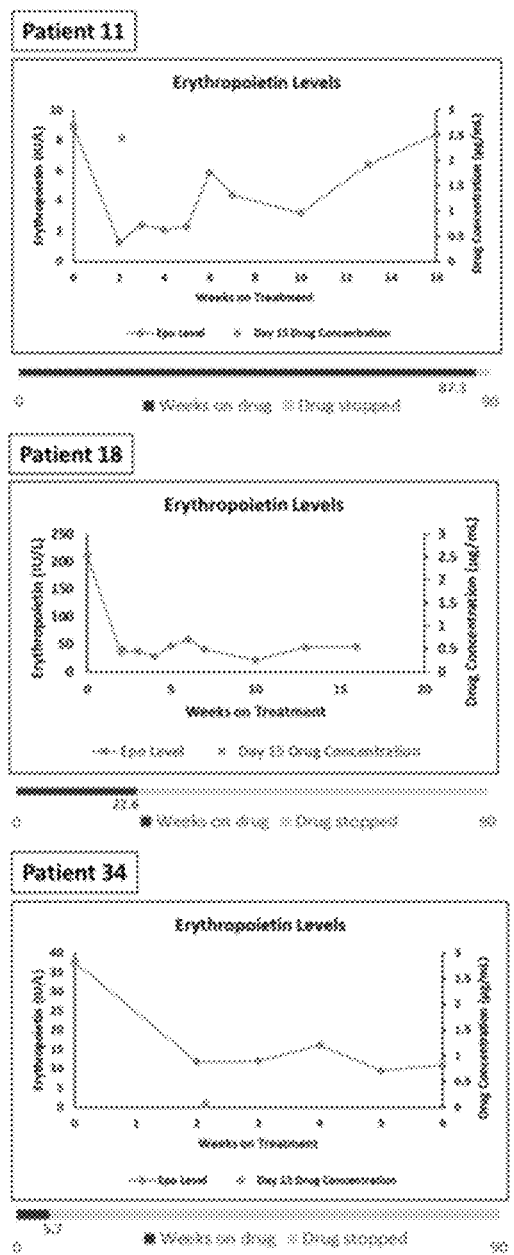
Figure 5D:
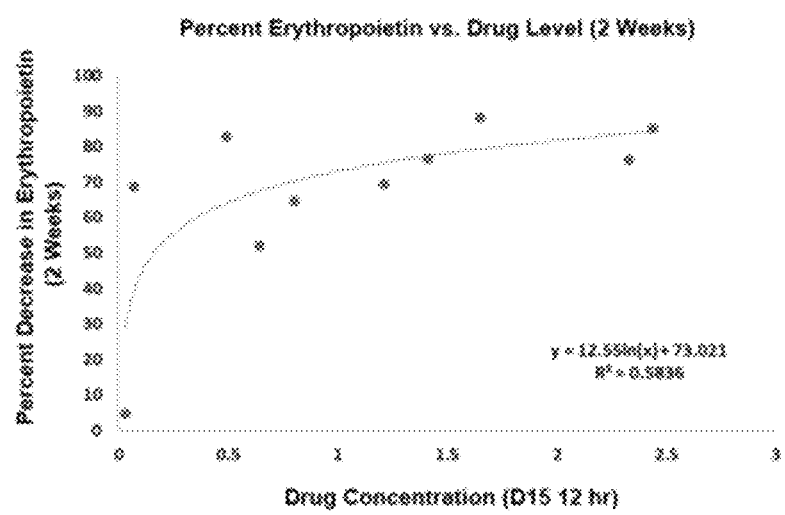
Figure 5E:
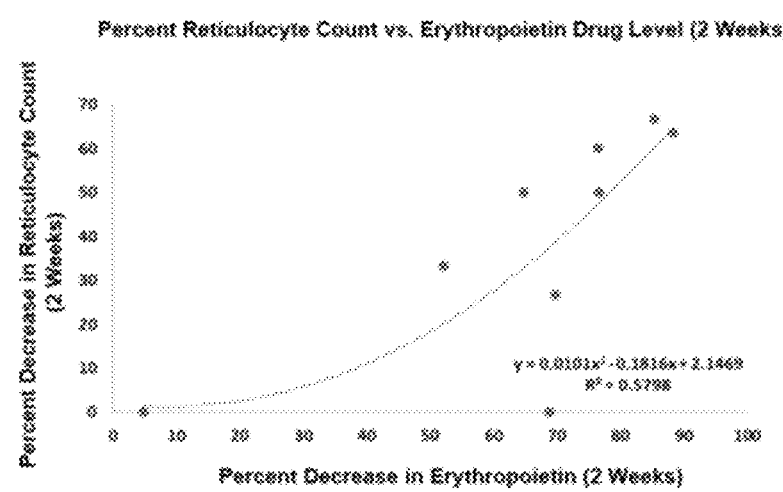

The effects of PT2385 on erythropoietin (EPO) over time were evaluated. EPO, which is secreted by kidney interstitial fibroblasts, is regulated by HIF-2 and may serve as a pharmacodynamic marker. A reduction in EPO at 2 weeks from baseline in 9 out of 10 patients was observed (FIG. 2A-G; FIG. 5C). The reduction in EPO had a logarithmic correlation with PT2385 levels at trough ($R^2=0.58$) (FIG. 5D). The observed decrease in EPO was functionally significant, and EPO levels were associated with a reduction in red blood cell precursors, reticulocytes, through a quadratic relationship ($R^2=0.58$) (FIG. 5E). Without being bound to any theory, a reduction of tumor EPO by itself may not be expected to reduce reticulocyte counts, so it is likely that the effect observed is due to inhibition of HIF-2 in kidney interstitial fibroblasts.

Figure 2F:
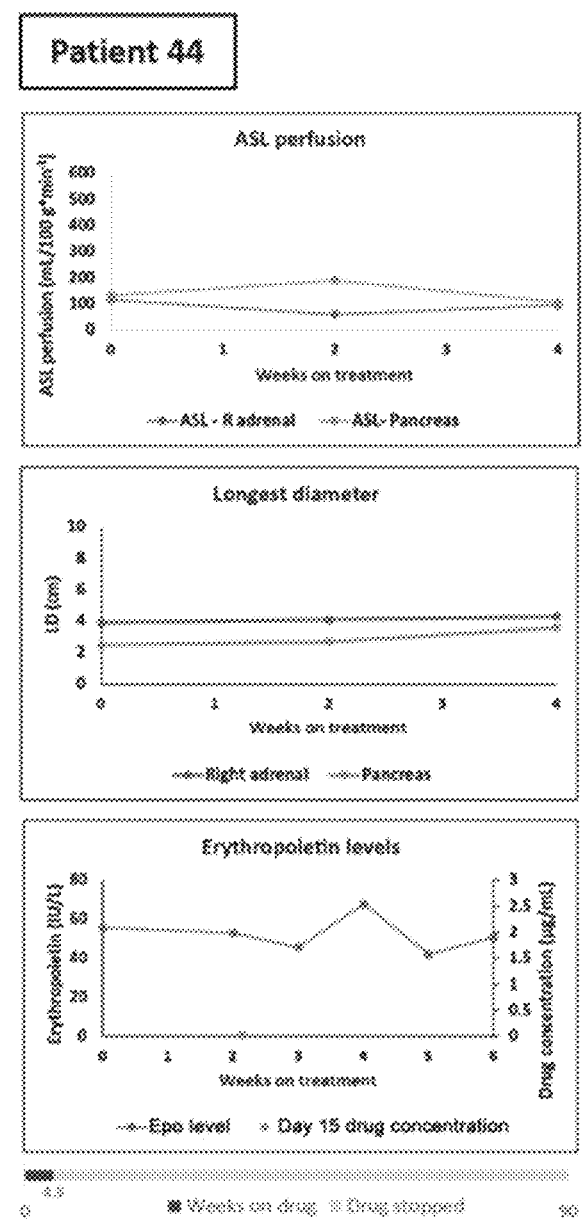
Figure 2G:
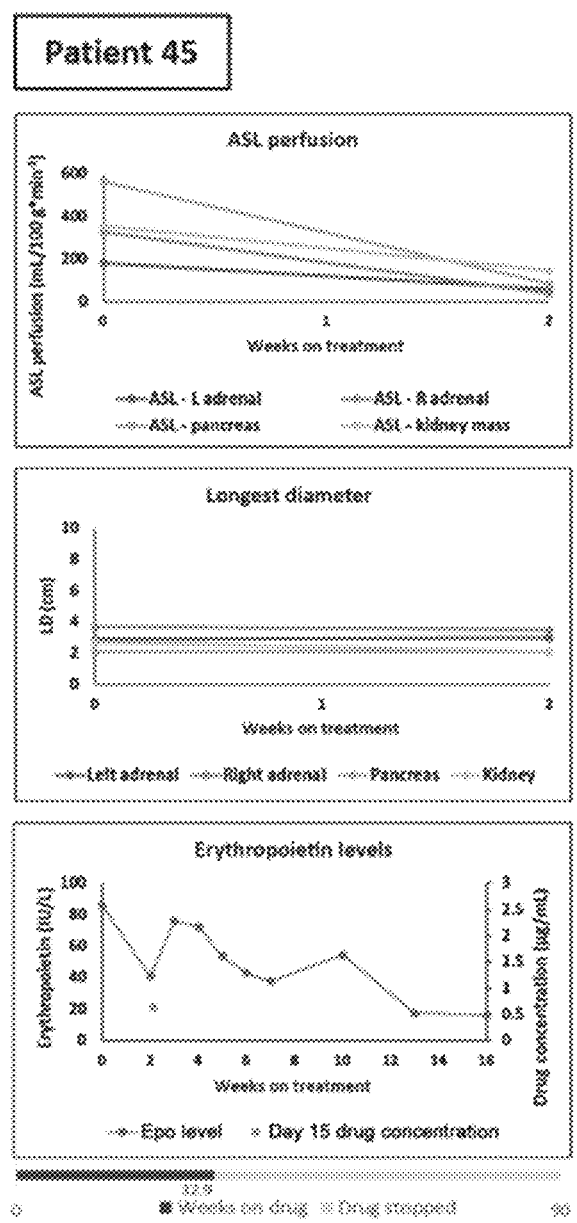

In one patient (Pt44), EPO levels failed to decrease following PT2385 administration (FIG. 2F). The patient received the recommended phase II dose (800 mg twice daily), but had the lowest trough levels of PT2385 across the whole cohort (0.03 µg/mL; FIG. 1 and FIG. 2). Thus, failure to achieve sufficient drug concentration in this patient may account for the failure to inhibit HIF-2. There were no significant changes in ASL perfusion and this patient progressed quickly, remaining on drug for less than 5 weeks (FIG. 2F). Overall, the data shows that HIF-2 was inhibited in non-tumor tissues in all but one patient, who likely achieved insufficient drug levels. Thus, at least as determined by HIF-2 inhibition in non-tumor tissues, adequate drug levels were achieved in all but one patient.

PT2385 Specifically Dissociates HIF-2 Complexes in ccRCC Metastases

Figure 3:
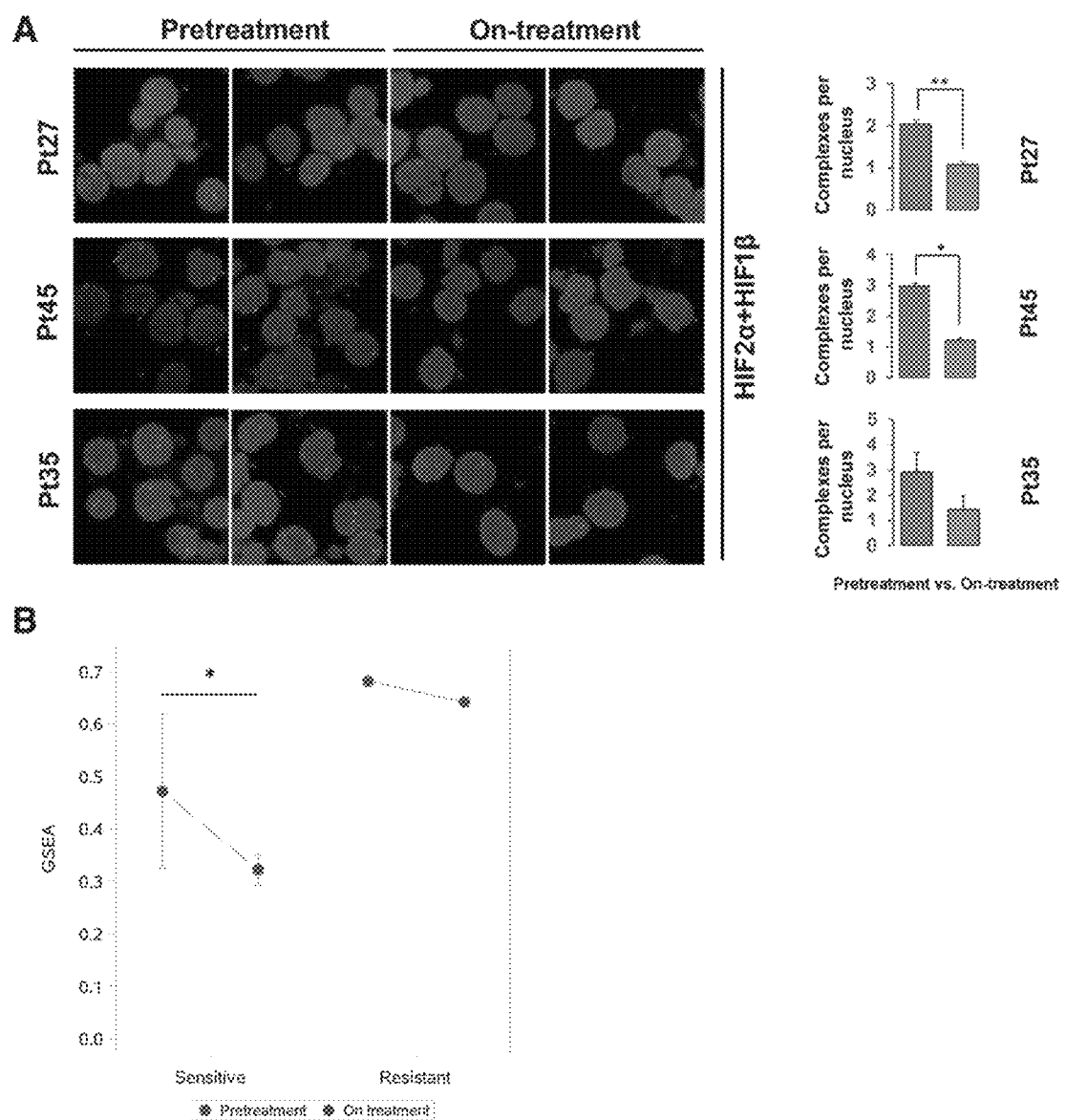
FIG. 3 panels A and B show the dissociation of HIF-2 complexes by PT2385, inhibiting HIF-2 target genes. Panel A shows the proximity ligation assay of HIF-2α/HIF-1β complexes from touchpreps of biopsies from metastases of patients at week 6/7 of PT2385 (while receiving drug) compared to biopsies taken prior to treatment initiation for Pt27, Pt45, and Pt35. Representative images and quantitative data are shown. Panel B shows gene set enrichment analysis for the HIF-2 target gene signature, comparing pre-treatment versus week 6/7 biopsy samples from two sensitive patients (Pt27, Pt45) and one resistant patient (Pt35; *, $P<0.05$; **, $P<0.01$).

To evaluate the effect of PT2385 on HIF-2 specifically in tumors, on-treatment tumor biopsies were used. Pre-treatment and on-treatment samples that were adequate were available for 3 patients (Pt27, Pt35, and Pt45). In all 3 patients, the same site was biopsied at baseline and while on drug. The drug was not discontinued for the biopsy procedure. A proximity ligation assay (PLA) was used to determine whether PT2385 dissociated HIF-2α/HIF-1β heterodimers. Antibodies against HIF-2α and HIF-1β conjugated with complementary oligonucleotides were used, which can amplify a signal (detected by fluorescence microscopy) if they are in physical proximity. HIF-2 complexes at baseline were readily detected and a statistically significant decrease in HIF-2 complexes in 2 out of the 3 patients (Pt27 and Pt45) was observed (FIG. 3A). In these two patients, HIF-1 complexes in parallel (HIF-1α/HIF-1β were examined. In contrast to the drug effect on HIF-2 complexes, similar levels of HIF-1 complexes were identified in pre-treatment and on-treatment samples (FIG. 7A). This data shows that PT2385 dissociates HIF-2 complexes in patient metastases and that the effect is specific for HIF-2.

Inhibition of HIF-2 Gene Expression Program by PT2385 in Tumors

The impact of PT2385 on HIF-2-dependent gene expression by RNA-Seq was measured next. Gene expression analyses in pre-treatment and on-treatment biopsies were performed. The HIF-2-dependent transcriptome in renal cancer were previously defined using tumorgrafts. RNA-Seq analyses identified 296 genes downregulated by the inhibitor compared to vehicle-treated tumorgrafts. Eliminating non-coding RNAs and genes with unclear annotation reduced this list to 277 genes, which were used for gene set enrichment analysis. A significant decrease in HIF-2 target genes in tumors from Pt27 and Pt45 was observed, but not Pt35 (FIG. 3B). This correlated with HIF-2 complex dissociation (FIG. 3A), and PT2385 activity in patients (FIG. 1). Whereas Pt27 and Pt45 derived prolonged benefit from PT2385 and remained on treatment for 32 and 32.9 weeks, respectively, Pt35 progressed after only 5 weeks (FIG. 1 and FIG. 2C-D&G). This data suggests that a reduction in HIF-2-dependent gene expression is necessary for PT2385 anti-tumor activity.

Figure 4A:
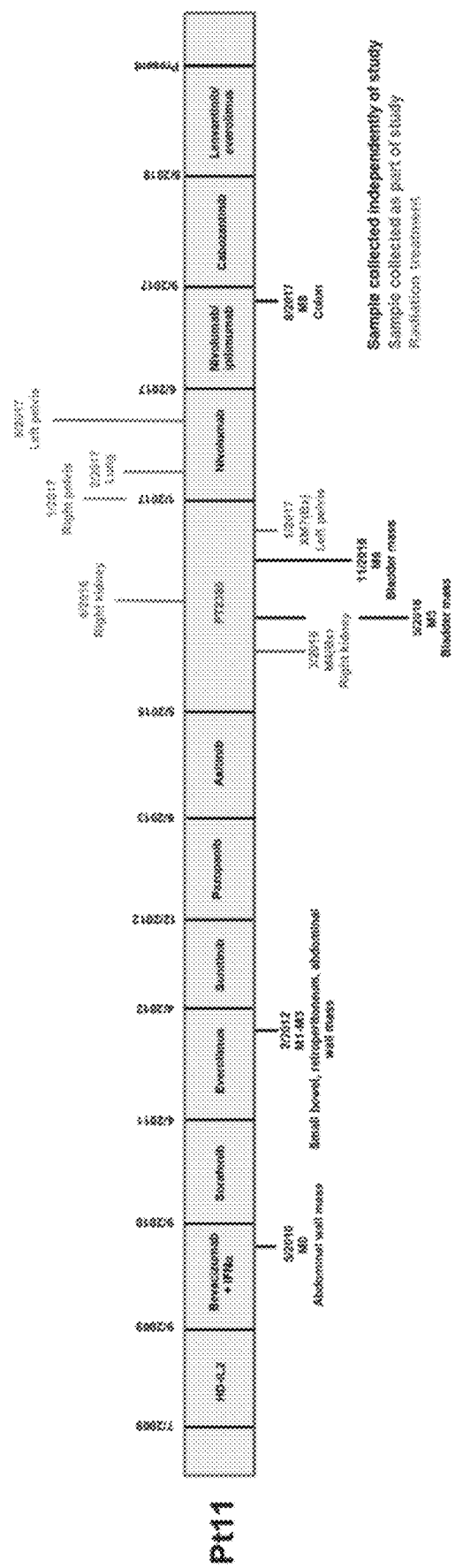
FIG. 4A-F shows the identification of a resistance mutation with preserved HIF-2 complex formation and target gene expression in a patient metastasis.
Figure 4B:
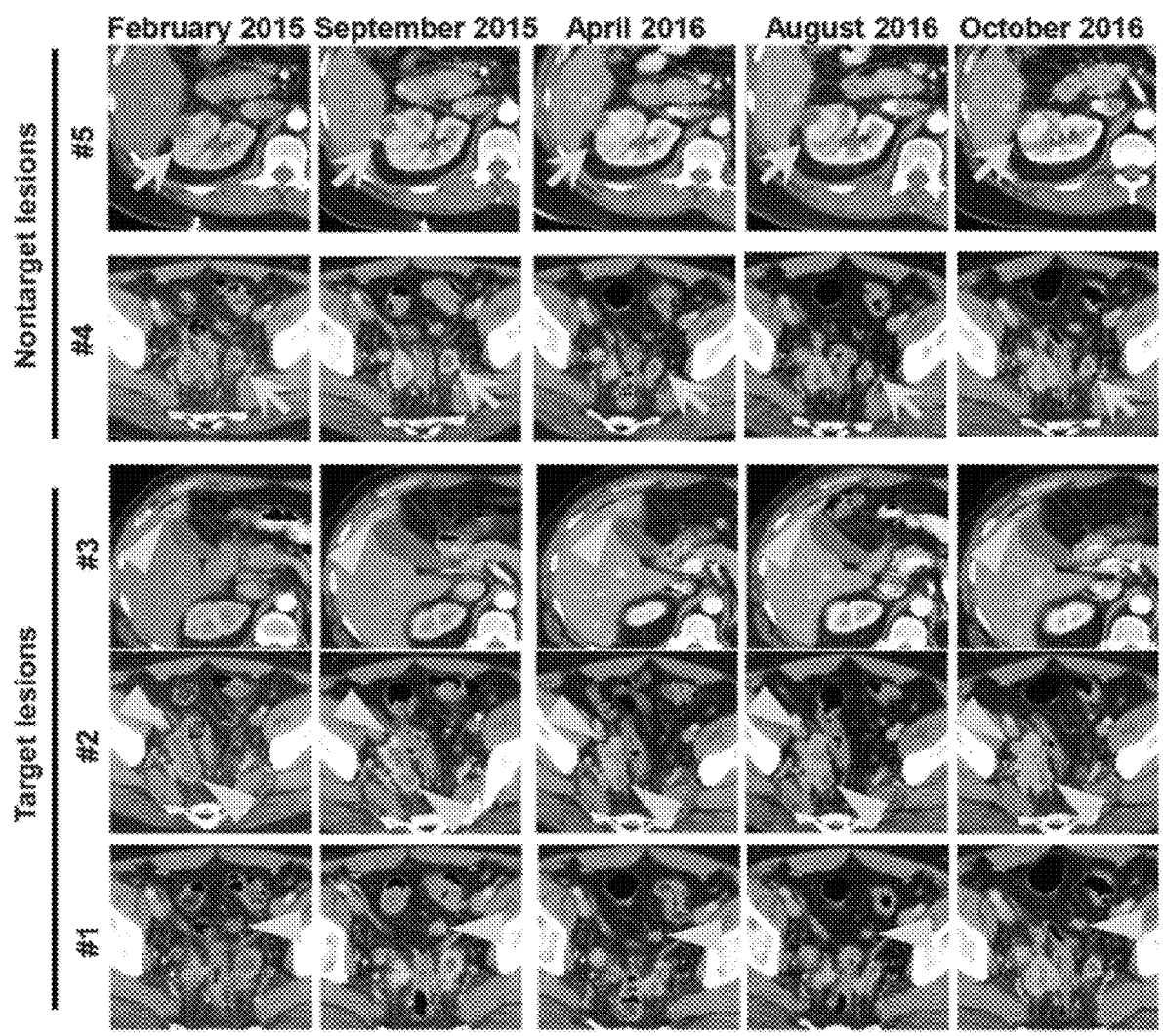

Identification of an Acquired Resistance Mutation in HIF-2α Reveals Core HIF-2 Dependency in ccRCC in Humans Pt11 enrolled in the dose-escalation part of the phase I trial and received 800 mg twice daily of PT2385, which became the recommended phase II dose (FIG. 4A). Pt11 had adequate circulating drug levels, as well as HIF-2 inhibition both in non-tumor tissues (85% reduction in EPO with a 67% reduction in reticulocytes; see FIG. 1; FIG. 5C) as well as in tumor tissues (FIG. 7B). Pt11 remained on treatment for 87.1 weeks with stable disease by RECIST 1.1 (FIG. 4B and FIG. 5C). This was remarkable as Pt11 had previously progressed on 7 lines of systemic therapy including multiple VEGF/VEGFR2 inhibitors. However, a mass in his remaining kidney (referred to as M4) progressed with increased enhancement, and it was biopsied as shown in FIG. 4A-B).

First, it was determined whether M4 represented a metastasis, or an independent primary tumor arising in the remaining kidney. Whole exome sequencing (WES) was performed and the mutations identified in M4 compared to other metastases from the same patient were evaluated. Multiple mutations were shared across metastases, which indicated a shared origin. Then mutations known to occur early during the process of RCC development were focused on. Mutations in both VHL and PBRM1, which were found in Pt11, are truncal mutations in ccRCC. The same VHL and PBRM1 mutations found in M4 were found in previously collected M0 (abdominal wall), M1 (small bowel) and M2 (retroperitoneum) metastases, which showed that all these metastases (collected over a span of 6 years) arose from the same primary tumor.

Figure 4C:
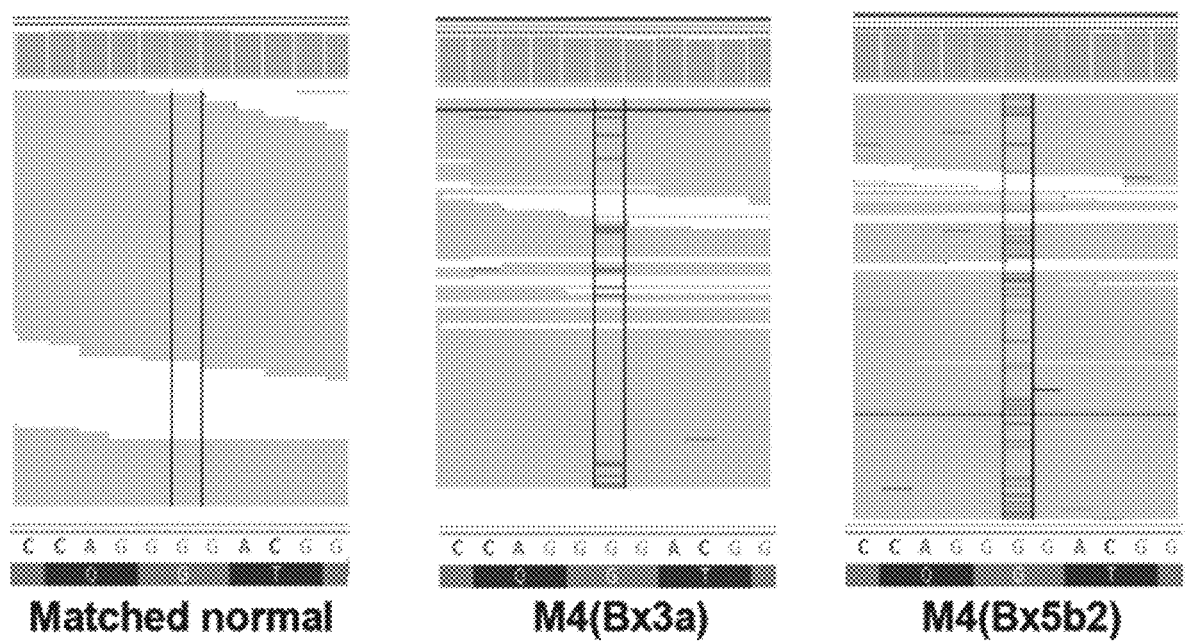
Figure 4D:
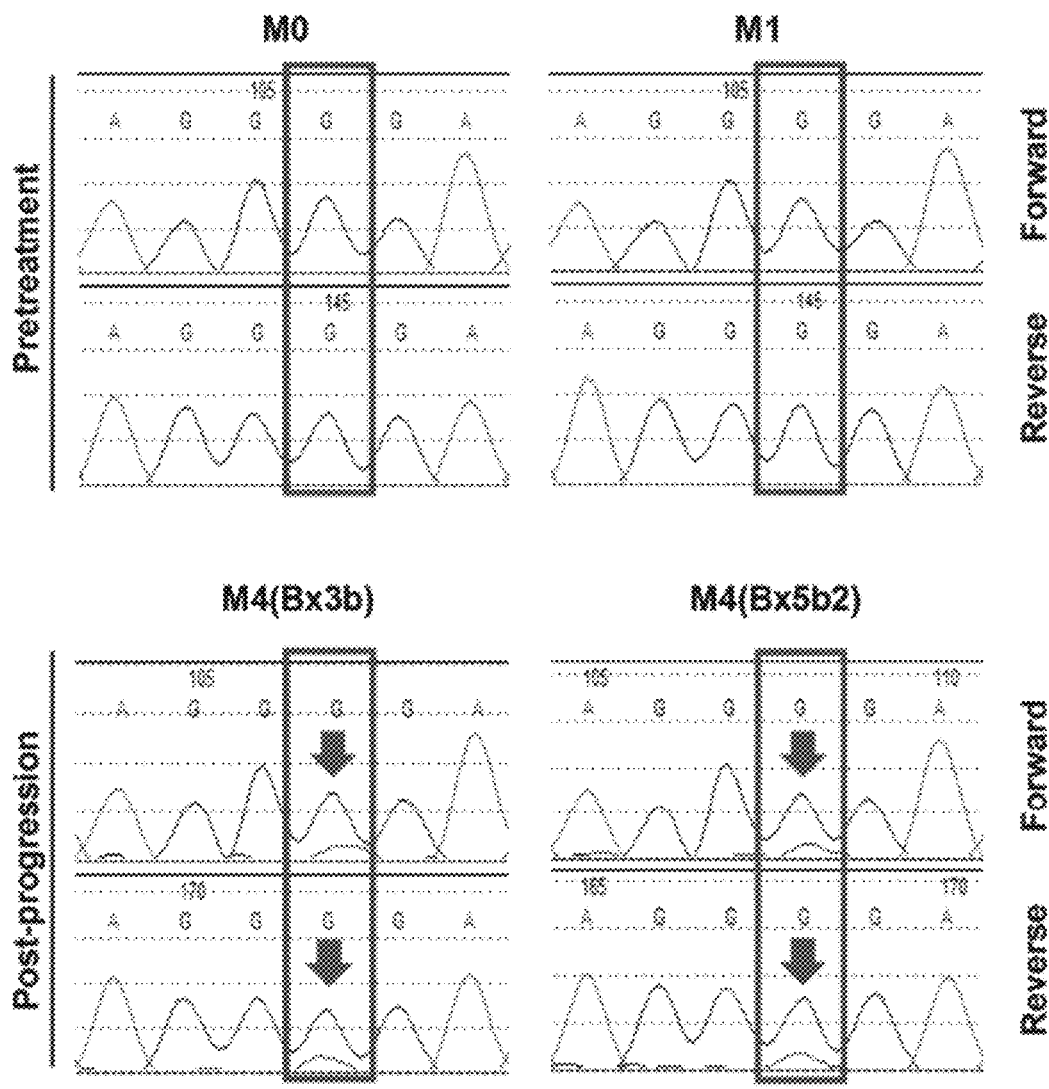

Next, the mechanism of resistance was determined. WES analyses of M4 identified a c.968G>A substitution in HIF2A (also called EPAS1). The mutation was detected in two tissue cores obtained during the same percutaneous computed tomography (CT)-guided biopsy procedure (FIG. 4C). There was no pre-treatment biopsy specifically for M4, but the mutation was not observed in 3 other previously resected metastases (M0, M1 and M2; FIG. 4D). Overall, these data suggest that the mutation was acquired late, after exposure to PT2385.

This was the same mutation previously identified when resistance to HIF-2 inhibitors using the close analog PT2399 in tumorgraft models (c.968G>A) was modeled. For these experiments, tumorgraft-bearing mice (from a different patient) were treated with PT2399 for over 6 months, until they developed resistance, and the tumors were then sequenced. The HIF2A c.968G>A mutation translates to a p.Gly323Glu, and Gly323 lies in the pocket bound by PT2385 and would be expected to interfere with drug binding.

Gatekeeper Mutation Preserves HIF-2 Complexes and Gene Expression

Figure 4E:
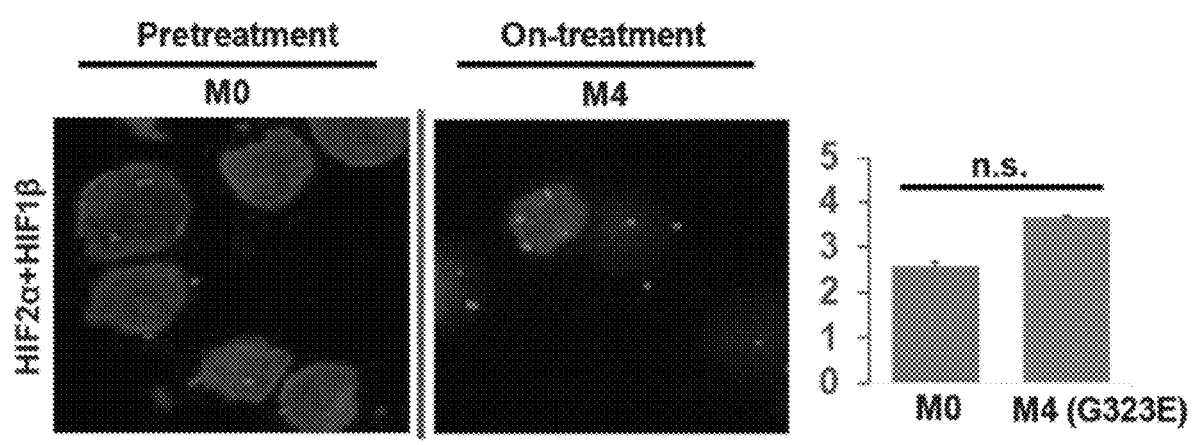

It was hypothesized that if the HIF-2α G323E mutation functioned as a gatekeeper, HIF-2 complexes should be preserved in the resistant kidney metastases, and proximity ligation assays were performed. As for other on-study biopsies, the procedure was performed while the patient remained on drug. As shown in FIG. 4E, the number of HIF-2 complexes detected in M4 was similar to an untreated metastasis (M0). Thus, it was concluded that the G323E substitution prevented HIF-2 dissociation by PT2385 in the renal metastasis. These results are in keeping with previous results in cells in culture showing that ectopic expression of HIF-2α G323E is sufficient to prevent drug-induced dissociation of HIF-2 complexes. This mutation has also been shown to interfere with drug binding in biochemical experiments. Overall, this data shows for the first time in humans that resistance to PT2385 treatment arises from the development of a gatekeeper mutation in HIF-2α.

Figure 4F:
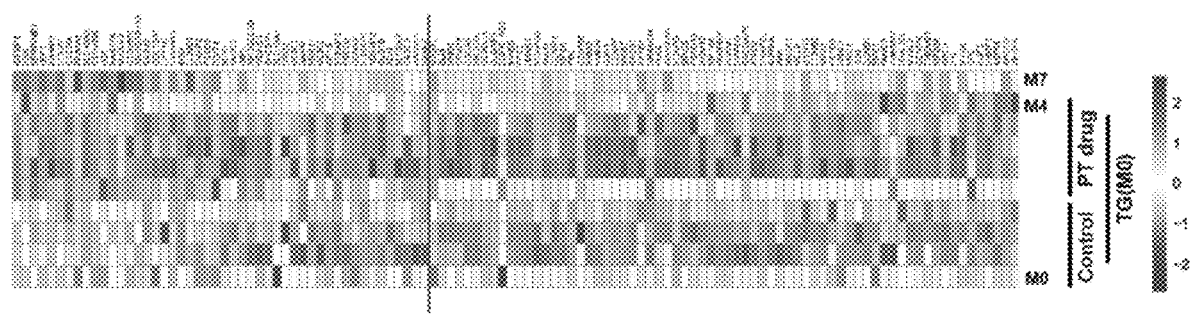

Next, the effects of the G323E mutation on HIF-2 target gene expression by RNA-Seq were examined. Genes downregulated by the HIF-2 inhibitor in a tumorgraft line that had been generated from this particular patient were focused on. Out of 277 genes evaluated (representing the HIF-2α gene signature), 170 were downregulated in tumorgrafts upon treatment with the related HIF-2 inhibitor PT2399 (FIG. 8). To extrapolate from mouse tumorgrafts, the list was narrowed by requiring that the expression of these genes be increased in an untreated tumor from the patient (M0), which left 116 genes (FIG. 4F and FIG. 8). This list corresponds to genes expressed in the patient tumor that are downregulated upon treatment with the HIF-2 inhibitor in corresponding tumorgrafts. The 116 genes in the M4 metastasis with the HIF-2α G323E mutation were then evaluated. Over 40% of the genes were expressed at levels comparable to control samples and were not downregulated by PT2385 (n=48; FIG. 4F and FIG. 8). The results, which may have been confounded by stromal contamination of the M4 biopsy samples, were highly statistically significant (p<0.0001). Further, among the 48 genes, 21 were expressed at levels comparable to untreated samples including several canonical HIF-2 target genes such as IGFBP1, LOX, and SERPINE1 (FIG. 4F and FIG. 8). Overall, this data shows that the HIF-2α G323E mutation interferes with PT2385-mediated inhibition of HIF-2 target genes in the resistant metastases.

Figure 9:
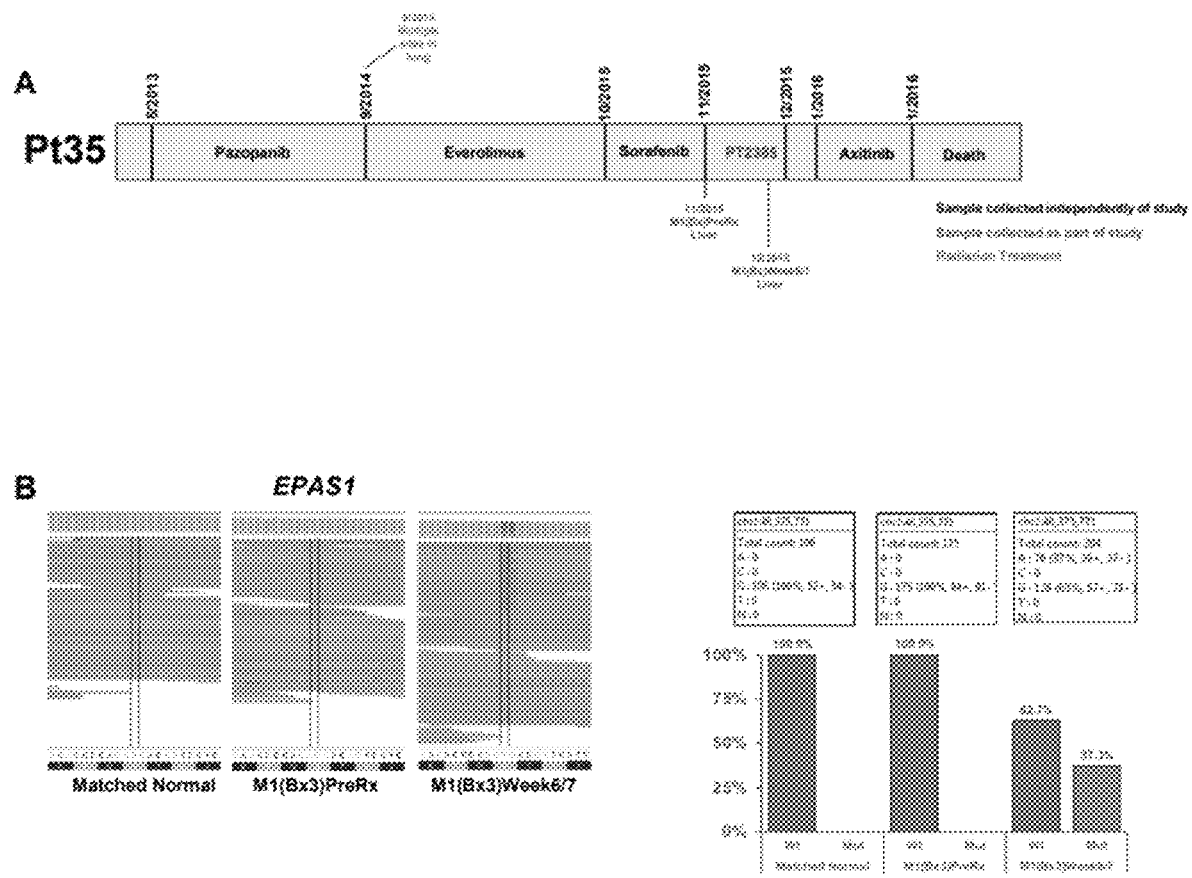
FIG. 9 Panels A-D show HIF-2α resistance mutation in Pt35 metastasis progressing on PT2385. Panel A shows treatment timeline of Pt35 including tumor resections and biopsies. Panel B shows WES reads of matched normal, pretreatment biopsy (PreRx), and on-treatment week 6/7 biopsy from the same liver metastasis (M1) showing in green the EPAS1 c.968G>A substitution (Adjacent base substitution in a subset of mutant M1 reads does not affect mutant codon), and a histogram with observed mutation frequencies. Panel C shows WES reads showing a TSC1 c.1525C>T substitution, and a histogram with observed mutation frequencies. Panel D shows WES reads showing a PBRM1 c.1300C>T substitution, and a histogram with observed mutation frequencies. Mutation frequencies shown are by manual inspection.
Figure 9:
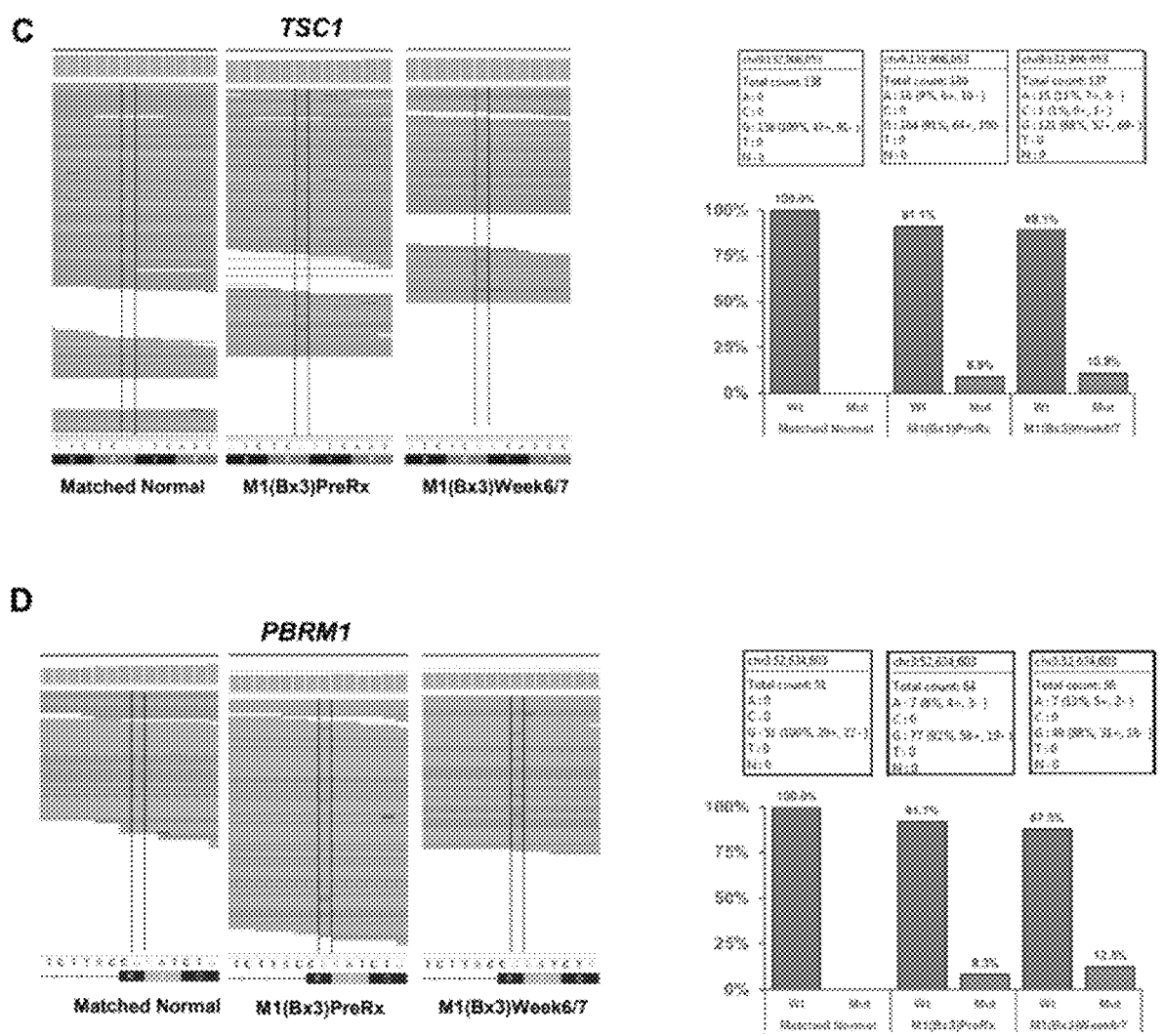

The same HIF2A mutation (c.968G>A; p.G323E) was identified in a second patient, Pt35. As for Pt11, Pt35 had adequate circulating drug levels and HIF-2 inhibition in non-tumor tissues (FIG. 1 and FIG. 2D). However, the finding of a HIF2A mutation in Pt35 was unexpected. Pt35 had progression after just 36 days on drug (FIG. 1, FIG. 9A), which was more in keeping with innate resistance, which we believed to evidence HIF-2-independent biology. In fact, the biopsy showing the mutation was the week 6/7 biopsy, on-treatment biopsy, which became the progression biopsy. Similarly unexpected was the finding that the mutation was absent from the pre-treatment biopsy, which was of the same site where the week 6/7 biopsy was obtained (a liver metastasis) (FIG. 9B). Other mutations were observed, and while some mutations, such as in TSC1, were observed across pretreatment and on-treatment/progression samples, others, such as a PBRM1 mutation, was only called by the algorithm in the progression samples. Manual review of the BAM files showed the PBRM1 mutation in both pretreatment and progression samples (FIGS. 9C-D), but the mutation was present at low frequency and thus not called by the algorithm. While the HIF2A mutation was found in the progression sample at significantly higher frequencies than the TSC1 and PBRM1 mutations, it is possible that the failure to detect it in the pre-treatment sample (even by manual review; FIG. 9B) is due to tumor heterogeneity and potentially tumor contamination by stromal or other cells, as the probability that this mutation would be an acquired mutation not pre-existing in the metastasis seems low (given the short time to progression). Independently, the presence of this mutation likely explains the persistence of HIF-2 complexes and preserved HIF-2 target gene expression despite PT2385 treatment (FIGS. 3A-B). Overall, this data shows that rapid acquisition of resistance may not always indicate target-independent biology and raises the possibility that resistance mutations may pre-exist in some patients at low frequency.

Other Potential Mechanisms of Resistance

Figure 10:
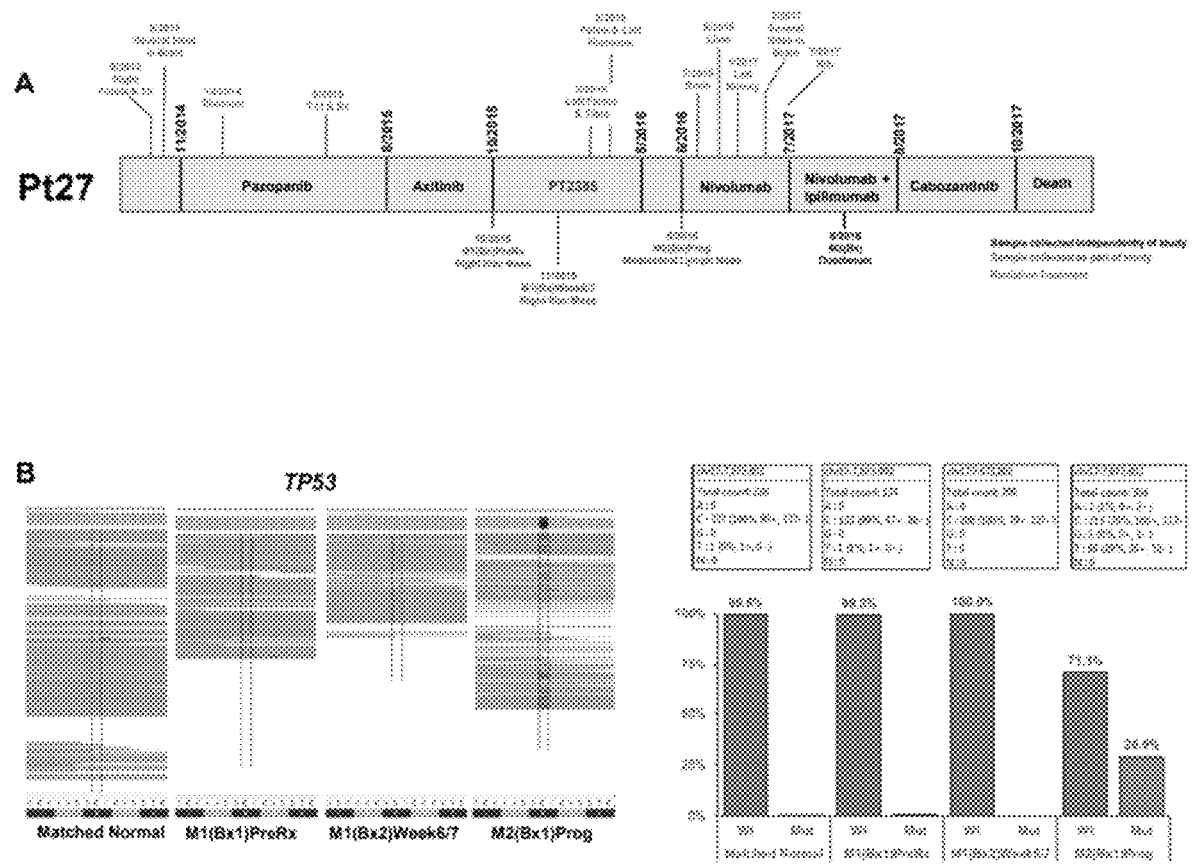
FIG. 10 Panels A-D show p53 mutation in Pt27 metastasis progressing on PT2385. Panel A shows treatment timeline of Pt27 including tumor resections and biopsies. Treatment with the HIF-2 inhibitor (PT2385) was from October 2015-May 2016. Panel B shows WES reads of matched normal, pretreatment biopsy (PreRx) and on week 6/7on-treatment biopsy of the same right iliac metastasis M1, and a progressing hilar/mediastinal lymph node metastasis M2 showing the TP53 c.818G>A substitution, and a histogram with observed mutation frequencies. Panel C shows a histogram with observed mutation frequencies for PBRM1 mutation. Panel D shows immunohistochemistry showing stabilization of the mutant p53 protein in the progressing metastasis M2 compared to pretreatment M1 sample. Mutation frequencies shown are by manual inspection.

There were suitable samples to evaluate resistance for one other patient, Pt27. Pt27 achieved appropriate circulating drug levels and HIF-2 inhibition in non-tumor tissues (FIG. 1 and FIG. 2C). Pt27 was sensitive to the HIF-2 inhibitor and remained free of progression for 220 days (FIG. 1; FIG. 10A). WES analyses of a site of progression failed to identify mutations in HIF2A (or HIF1B, which we previously also linked to resistance in tumorgraft models). A TP53 mutation (c.818G>A; p.R273H) was identified (FIG. 10B). The p53 R273H mutation is a well-validated tumor-promoting mutation extensively reported as somatically acquired in tumors. While the mutation was significantly enriched in the progression biopsy compared to pre-treatment and on-treatment biopsies (FIG. 10B), the interpretation was confounded by the fact that pre-treatment and on-treatment biopsies had scant tumor cells (as determined also by the evaluation of VHL and PBRM1 mutations) (FIG. 10C). To assess whether the mutation may be acquired, immunohistochemistry (IHC) was looked at. TP53 mutations are often associated with protein stabilization, which can be scored by IHC. p53 IHC analyses showed low signal in tumor cells in the pre-treatment biopsy sample, and high signal in two progression biopsy cores from the same progression metastasis (FIG. 10D). Overall, this data is consistent with the notion that the TP53 mutation was acquired coincidentally with the development of resistance, and raise the possibility that p53, as previously postulated based on cell line analyses in tissue culture, may also be implicated in resistance to HIF-2 inhibitors.

Overall, these findings demonstrate a core dependency on HIF-2 in metastatic ccRCC, and establish PT2385 as a highly specific HIF-2 inhibitor in humans.

We claim:

1. A method of treating cancer in a patient comprising determining if cancerous cells of the patient have a HIF2A, HIF1B, or TP53 resistance mutation, and:
    (i) if not, then treating the patient with an HIF-2 inhibitor; and
    (ii) if so, then treating the patient with one or more therapies other than an HIF-2 inhibitor, thereby treating cancer in the patient.

2. The method of claim 1, wherein where the patient is treated with an HIF-2 inhibitor, further treating the patient with one or more additional therapies.

3. The method of claim 1, wherein the one or more therapies other than an HIF-2 inhibitor comprise chemotherapy, cancer immunotherapy, surgical removal of all or part of the cancerous tissue, or radiation therapy.

4. The method of claim 1, wherein the resistance mutation results in an amino acid substitution in one or more of HIF2α, HIF1β, or p53 proteins.

5. The method of claim 1, wherein the resistance mutation results in a G323E amino acid substitution in HIF2α.

6. The method of claim 1, wherein the resistance mutation results in a F446L amino acid substitution in HIF1β.

7. The method of claim 1, wherein the resistance mutation results in a R273H amino acid substitution in p53.

8. The method of claim 1, wherein the HIF-2 inhibitor is PT2385.

9. The method of claim 1, wherein the HIF-2 inhibitor is PT2977.

10. The method of claim 1, wherein the patient is a mammal.

11. The method of claim 1, wherein the cancerous cells are kidney cells.

12. The method of claim 1, wherein the cancerous cells are bladder cancer cells, breast cancer cells, colon cancer cells, rectal cancer cells, endometrial cancer cells, leukemia cells, liver cancer cells, lung cancer cells, melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

13. A method of screening of a drug comprising, contacting a drug with cancerous cells having one or more HIF2A, HIF1B, or TP53 resistance mutations and determining if the drug detrimentally affects metabolism or growth of the cancerous cells, wherein if the drug detrimentally affects metabolism or growth of the cancerous cells, then is it selected for further testing.

14. The method of claim 13, wherein the cancerous cells are kidney cells.

15. The method of claim 13, wherein the cancerous cells are bladder cancer cells, breast cancer cells, colon cancer cells, rectal cancer cells, endometrial cancer cells, leukemia cells, liver cancer cells, lung cancer cells, melanoma cells, non-Hodgkin lymphoma cells, pancreatic cancer cells, prostate cancer cells, thyroid cancer cells, parathyroid cancer cells, neuroblastoma cancer cells, lymphoma cancer cells, adrenocortical cancer cells, sarcoma cells, bile duct cancer cells, brain cancer cells, bone cancer cells, gastrointestinal cancer cells, cardiac cancer cells, cervical cancer cells, chronic myeloproliferative neoplasm cells, esophageal cancer cells, head and neck cancer cells, retinoblastoma cells, gall bladder cancer cells, testicular cancer cells, ovarian cancer cells, or laryngeal cancer cells.

16. The method of claim 13, wherein the resistance mutation results in an amino acid substitution in one or more of HIF2α, HIF1β, or p53 proteins.

17. The method of claim 13, wherein the resistance mutation results in a G323E amino acid substitution in HIF2α.

18. The method of claim 13, wherein the resistance mutation results in a F446L amino substitution in HIF1β.

19. The method of claim 13, wherein the resistance mutation results in a R273H amino acid substitution in p53.

20. The method of claim 1, wherein the patient has previously been treated with the HIF-2 inhibitor.

* * * * *